US009630938B2

(12) United States Patent
Brown et al.

(10) Patent No.: US 9,630,938 B2
(45) Date of Patent: Apr. 25, 2017

(54) METHOD OF SYNTHESIS OF SUBSTITUTED HEXITOLS SUCH AS DIANHYDROGALACTITOL

(71) Applicant: DELMAR PHARMACEUTICALS, INC., Vancouver (CA)

(72) Inventors: Dennis M. Brown, Menlo Park, CA (US); Mike Tso-Ping Li, Cupertino, CA (US)

(73) Assignee: DELMAR PHARMACEUTICALS, INC., Vancouver (CA)

( * ) Notice: Subject to any disclaimer, the term of this patent is extended or adjusted under 35 U.S.C. 154(b) by 0 days.

(21) Appl. No.: 14/550,131

(22) Filed: Nov. 21, 2014

(65) Prior Publication Data

US 2015/0329511 A1    Nov. 19, 2015

Related U.S. Application Data

(63) Continuation-in-part of application No. 14/072,603, filed on Nov. 5, 2013, now Pat. No. 9,085,544, which
(Continued)

(51) Int. Cl.
*C07D 493/00* (2006.01)
*C07D 301/24* (2006.01)
(Continued)

(52) U.S. Cl.
CPC ............ *C07D 301/24* (2013.01); *C07C 29/62* (2013.01); *C07D 303/14* (2013.01); *C07D 493/04* (2013.01)

(58) Field of Classification Search
CPC .. C07D 301/24; C07D 303/14; C07D 493/00; C07C 29/62
(Continued)

(56) References Cited

U.S. PATENT DOCUMENTS 3,470,179 A    9/1969  Ott
5,417,911 A    5/1995  Mayer et al.
(Continued)

FOREIGN PATENT DOCUMENTS

HU          3863          3/1972
JP        616679          1/1994
WO    2012/024367 A2     2/2012

OTHER PUBLICATIONS

M. Jarman & W.C.J. Ross, "The Formation of Epoxides from Substituted Hexitols," Carbohydrate Res. 9: 139-147 (1969), 10 pages.
(Continued)

*Primary Examiner* — T. Victor Oh
(74) *Attorney, Agent, or Firm* — Ditthavong & Steiner, P.C.

(57) ABSTRACT

The present invention provides an efficient method of synthesizing and purifying dianhydrohexitols such as dianhydrogalactitol. In general, as applied to dianhydrogalactitol, the method comprises: (1) reacting dulcitol with a concentrated solution of hydrobromic acid at a temperature of about 80° C. to produce dibromogalactitol; (2) reacting the dibromogalactitol with potassium carbonate in t-butanol to produce dianhydrogalactitol; and (3) purifying the dianhydrogalactitol using a slurry of ethyl ether to produce purified dianhydrogalactitol. Another method produces dianhydrogalactitol from dulcitol; this method comprises: (1) reacting dulcitol with a reactant to convert the 1,6-hydroxy groups of dulcitol to an effective leaving group to generate an intermediate; and (2) reacting the intermediate with an inorganic weak base to produce dianhydrogalactitol through an intramolecular $S_N2$ reaction. Other methods for the synthesis of dianhydrogalactitol from dulcitol are described.

27 Claims, 5 Drawing Sheets

Related U.S. Application Data is a continuation-in-part of application No. 13/933,751, filed on Jul. 2, 2013, now Pat. No. 8,921,585, which is a continuation-in-part of application No. 13/817,046, filed as application No. PCT/US2011/048032 on Aug. 17, 2011, now Pat. No. 8,563,758.

(60) Provisional application No. 61/401,710, filed on Aug. 18, 2010.

(51) Int. Cl.
  *C07C 29/62* (2006.01)
  *C07D 303/14* (2006.01)
  *C07D 493/04* (2006.01)

(58) Field of Classification Search
  USPC .......................................... 514/475; 549/464
  See application file for complete search history.

(56) References Cited

U.S. PATENT DOCUMENTS

| | | |
|---|---|---|
| 7,157,079 B2 | 1/2007 | Nielsen et al. |
| 2002/0032230 A1 | 3/2002 | Pal et al. |
| 2002/0037328 A1 | 3/2002 | Brown |

OTHER PUBLICATIONS

Samoylova et al., Substances With Complexing Ability, Zh. Obsch. Chem. 43: 365-369 (1973), originally in Russian, provided with English translation, 11 pages.

METHOD OF SYNTHESIS OF SUBSTITUTED HEXITOLS SUCH AS DIANHYDROGALACTITOL

CROSS-REFERENCES

This application claims the benefit and is a continuation-in-part of U.S. patent application Ser. No. 14/072,603, by Dennis M. Brown, Ph.D. and Mike Li, filed Nov. 5, 2013, and entitled "Method of Synthesis of Substituted Hexitols Such as Dianhydrogalactitol," which in turn claimed the benefit and was a continuation-in-part of U.S. patent application Ser. No. 13/933,751, by Dennis M. Brown, Ph.D., filed Jul. 2, 2013, and entitled "Method of Synthesis of Substituted Hexitols Such as Dianhydrogalactitol," which in turn claimed the benefit and was a continuation-in-part of U.S. patent application Ser. No. 13/817,046, by Dennis M. Brown, Ph.D., filed Feb. 14, 2013, and entitled "Method of Synthesis of Substituted Hexitols Such as Dianhydrogalactitol," which in turn claimed the benefit of PCT Application Serial No. PCT/US2011/048032, by Dennis M. Brown, Ph.D., filed Aug. 17, 2011, designating the United States, and entitled "Method of Synthesis of Substituted Hexitols Such as Dianhydrogalactitol," which in turn claimed the benefit of U.S. Provisional Application Ser. No. 61/401,710, by Dennis M. Brown, Ph.D., filed Aug. 18, 2010, and entitled "Method of Synthesis of Substituted Hexitols Such as Dianhydrogalactitol." These five applications are incorporated herein in their entirety by this reference.

TECHNICAL FIELD OF THE INVENTION

The present invention is directed to improved methods for the synthesis of substituted hexitols, especially dianhydrogalactitol.

BACKGROUND OF THE INVENTION

A number of substituted hexitols, such as dianhydrogalactitol, have pharmacological activities. In particular, dianhydrogalactitol has been suggested for use in chemotherapy, such as in U.S. Pat. No. 7,157,059 to Nielsen et al., incorporated herein by this reference.

However, current methods of synthesis of such substituted hexitols, such as dianhydrogalactitol, are inefficient, and improved methods of synthesis of these substituted hexitols are required in order to provide larger quantities of these compounds for clinical use.

There is a particular need to be able to scale up these processes to produce large quantities of these substituted hexitols for pharmacological use and for the preparation of pharmaceutical compositions.

SUMMARY OF THE INVENTION

An improved method of synthesis of dianhydrohexitols such as dianhydrogalactitol comprises conversion of the hexitol to a dibromohexitol by reaction with concentrated hydrobromic acid, followed by conversion of the dibromohexitol to the dianhydrohexitol by reaction with potassium carbonate.

In general, as applied to the synthesis of dianhydrogalactitol, the method comprises the steps of:

(1) reacting dulcitol with a concentrated solution of hydrobromic acid at a temperature of about 80° C. to produce dibromogalactitol;

(2) reacting the dibromogalactitol with potassium carbonate in t-butanol to produce dianhydrogalactitol; and (3) purifying the dianhydrogalactitol using a slurry of ethyl ether to produce purified dianhydrogalactitol.

In this method, typically, the concentrated solution of hydrobromic acid is about 70% hydrobromic acid and is produced by reacting phosphorus with bromine in hydrobromic acid at elevated temperature. Typically, the dibromogalactitol is dissolved in t-butanol in a proportion of about 1 g of dibromogalactitol to 10 mL of t-butanol.

In this method, typically, the dulcitol is purified from the plant *Maytenus confertiflora* by the steps of:

(a) soaking the plant *Maytenus confertiflora* in a soaking solution of from about 50% to about 80% of ethanol for about 24 hours;

(b) collecting the soaking solution from step (a);

(c) repeating the soaking step of step (a) with a fresh soaking solution of from about 50% to about 80% of ethanol for about 24 hours;

(d) collecting the soaking solution from step (c) and combining it with the soaking solution collected in step (b);

(e) removing the solvent from the combined soaking solutions of step (d) by heating under reduced pressure to produce a concentrated solution;

(f) allowing the concentrated solution of step (e) to settle overnight and collecting the clear supernatant;

(g) extracting the clear supernatant from step (f) with chloroform and then removing the chloroform under heat and reduced pressure;

(h) dissolving the residue from step (g) in hot methanol and then cooling to allow crystallization; and (i) collecting the collected crystals of dulcitol, filtering, and drying the crystals under reduced pressure.

Although this method is described for the synthesis and purification of dianhydrogalactitol, it is not limited to dianhydrogalactitol, and can be applied to other hexitols bearing two epoxide groups such as substituted dianhydrogalactitols.

More generally, a method according to the present invention for synthesizing and purifying a dianhydrohexitol comprises the steps of:

(1) reacting a hexitol with a concentrated solution of hydrobromic acid at a temperature of about 80° C. to produce a dibromohexitol;

(2) reacting the dibromohexitol with a alkali metal salt of carbonate in a tertiary alcohol to produce a dianhydrohexitol; and (3) purifying the dianhydrohexitol using a slurry of an ether to produce the purified dianhydrohexitol.

Typically, the dianhydrohexitol is selected from the group consisting of dianhydrogalactitol and a substituted dianhydrogalactitol. Preferably, the dianhydrohexitol is dianhydrogalactitol.

Typically, the concentrated solution of hydrobromic acid is about 70% hydrobromic acid and is produced by reacting phosphorus with bromine in hydrobromic acid at elevated temperature.

Typically, the tertiary alcohol is selected from the group consisting of t-butanol, 2-methyl-2-butanol, and 3-ethylpentanol. Preferably, the tertiary alcohol is t-butanol.

Typically, the dibromohexitol is dissolved in the tertiary alcohol in a proportion of about 1 g of dibromohexitol to 10 mL of tertiary alcohol.

Typically, the dibromohexitol is purified by recrystallization prior to its conversion to dianhydrohexitol.

Typically, the alkali metal salt of carbonate is selected from the group consisting of sodium carbonate and potassium carbonate. Preferably, the alkali metal salt of carbonate is potassium carbonate.

Typically, the ether is an aliphatic ether with lower alkyl groups. Preferably, the ether is selected from the group consisting of dimethyl ether, methyl ethyl ether, diethyl ether, dipropyl ether, methyl propyl ether, and ethyl propyl ether. More preferably, the ether is diethyl ether.

Other methods for the synthesis of dianhydrogalactitol are described. In general, these methods start with dulcitol.

In one alternative, the method comprises:

(1) reacting dulcitol with a reactant to convert the 1,6-hydroxy groups of dulcitol to an effective leaving group to generate an intermediate; and (2) reacting the intermediate with an inorganic weak base to produce dianhydrogalactitol through an intramolecular $S_N2$ reaction.

Typically, the effective leaving group of step (1) is selected from the group consisting of Br, OTf (triflate or trifluoromethane sulfonate), and OTs (tosylate). Preferably, the effective leaving group of step (1) is Br.

In one alternative, the intermediate of step (1) is prepared by:

(a) using 45-48% aqueous hydrobromic acid with the addition of phosphorus and $Br_2$ to generate a 60-70% solution of hydrobromic acid, then adding dulcitol and reacting at 70° C. for 5-7 hours;

(b) cooling the reaction mass of (i) to room temperature and pouring into ice water to obtain the crude intermediate of step (1); and (c) recrystallizing using a polar solvent without a nucleophilic property.

In another alternative, the intermediate of step (1) is prepared by:

(a) adding dulcitol to a 62% aqueous hydrobromic acid solution and reacting at 70° C. for 5-7 hours;

(b) cooling the reaction mass of (a) to room temperature and pouring into ice water to obtain the crude intermediate of step (1); and (c) recrystallizing using a polar solvent without a nucleophilic property.

In yet another alternative, the intermediate of step (1) is prepared by:

(a) adding dulcitol to a 33% HBr solution in acetic acid and mixing for 5-7 hours at room temperature;

(b) adding methanol and mixing for 15 hours;

(c) concentrating under vacuum to remove most of the solvent;

(d) recrystallizing using a polar solvent without a nucleophilic property.

In still another alternative, the intermediate of step (1) is prepared by:

(a) dissolving dulcitol in pyridine or dimethylformamide (DMF) at room temperature;

(b) adding $CBr_4$ and $Ph_3P$ in sequence and mixing for 15-18 hours at room temperature;

(c) after the completion of the reaction of step (ii), concentrating under vacuum to remove solvent and chloroform formed from the reaction;

(d) washing the remaining solid several times with dichloromethane to remove triphenylphosphine byproduct; and (e) recrystallizing using a polar solvent without a nucleophilic property. Typically, in this alternative, the dulcitol is dissolved in pyridine. Alternatively, the dulcitol is dissolved in dimethylformamide.

Typically, the polar solvent without a nucleophilic property is selected from the group consisting of 2-chloromethane/t-butanol and 2-chloromethane/isopropyl alcohol.

When the effective leaving group of step (1) is selected from the group consisting of OTf (triflate or trifluoromethane sulfonate) and OTs (tosylate), typically, the intermediate is generated by:

(a) dissolving dulcitol in pyridine;

(b) adding TsCl or $Tf_2O$ at 0° C. and mixing for 15-18 hours;

(c) after the completion of the reaction, concentrating under vacuum to remove solvent;

(d) pouring the remaining solution into ice water to obtain the intermediate; and (e) recrystallizing using a polar solvent without a nucleophilic property.

In one alternative, the intermediate is converted to DAG using $K_2CO_3$ and t-BuOH.

In another alternative, the intermediate is converted to DAG using an inorganic alkali in a polar nonionic solvent. In this alternative, typically, the intermediate is converted to DAG employing a process with the steps of:

(a) dissolving the intermediate in the polar nonionic solvent;

(b) adding an inorganic carbonate and mixing at room temperature for 5-7 hours;

(c) after the completion of the reaction of step (ii), adding p-toluenesulfonic acid to neutralize the inorganic carbonate;

(d) concentrating under vacuum to remove the solvent;

(e) washing the remaining solid with water to remove impurities;

(f) adding ether to the crude material of step (v); and (g) filtering the slurry to obtain DAG.

Typically, the inorganic carbonate is selected from the group consisting of $K_2CO_3$ and $Cs_2CO_3$. Preferably, the inorganic carbonate is $K_2CO_3$. Typically, the polar nonionic solvent is dimethylformamide (DMF).

Another aspect of the invention is a method for synthesizing dianhydrogalactitol (DAG) comprising the steps of:

(1) substituting the 1,6-hydroxyl groups of dulcitol with bromine;

(2) substituting the hydroxyl groups of dulcitol other than the 1,6-hydroxyl groups with acetyl groups to yield an intermediate in which the 1,6-hydroxyl groups of dulcitol are substituted with bromine and the hydroxyl groups of dulcitol other than the 1,6-hydroxyl groups are substituted with acetyl groups;

(3) reacting the intermediate of step (2) with zinc in the presence of an organic base to form double bonds through an elimination reaction;

(4) removing the protective acetyl groups; and (5) forming dianhydrogalactitol by the Sharpless epoxidation reaction.

Typically, the organic base is sodium methoxide. Typically, the substitution of the 1,6 hydroxy groups is performed with reaction with acetyl bromide. Typically, the acetylation of the hydroxy groups other than the 1,6-hydroxy groups is performed with acetic anhydride in pyridine.

Yet another method for the production of dianhydrogalactitol from dulcitol provides recrystallized dianhydrogalactitol of high quality. This method is suitable for scaling up and for the production of large quantities of recrystallized dianhydrogalactitol. This method can be applied to other hexitols.

In general, as applied to the synthesis of a dianhydrohexitol, the method comprises the steps of:

(1) converting a hexitol to a dibromo derivative of the hexitol by reaction of the dulcitol with hydrobromic acid for from about 12 hours to about 36 hours at an elevated temperature;

(2) adding the product of step (1) to water, agitating the product of step (1) added to water for from about 18 hours to about 36 hours, filtering the mixture of the product of step (1) and water, washing the mixture with a large volume of water, drying the solid product under nitrogen, and then subsequently washing the dried solid product with a large volume of an aliphatic ether;

(3) reacting the product of step (b) with a carbonate of an alkali salt in a polar aprotic solvent at an elevated temperature;

(4) filtering the product of step (3) to remove the solids;

(5) washing the solids removed in step (4) with a polar aprotic solvent and combining the washings with the solids removed in step (4);

(6) concentrating the combination of the washings with the solids of step (5) to a volume that is approximately from about 0.20 to about 0.27 of the volume of polar aprotic solvent used in step (3) at a temperature of from about 30° C. to about 40° C.;

(7) agitating the concentrated product of step (6) for from about 18 hours to about 36 hours at a temperature of from about 0° C. to about 10° C.;

(8) washing the product of step (7) with an aliphatic ether;

(9) drying the washed product of step (8) under nitrogen; and

(10) recrystallizing the product of step (9) by:
(a) dissolving the product of step (9) in acetone;
(b) filtering off insoluble solids remaining after dissolving the product of step (9) in acetone;
(c) concentrating the solution of step (10)(a) down to a volume of about 0.07 to about 0.12 of the original volume of acetone;
(d) cooling the concentrated solution of step (10)(c) to about −20° C. to generate solid recrystallized dianhydrohexitol and agitating the suspension of solid recrystallized dianhydrohexitol for from about 18 hours to about 36 hours;
(e) filtering the solids of step (10)(d) and washing the solids with a large volume of an aliphatic ether; and
(f) drying the washed solids of step (10)(e) under nitrogen to produce a solid recrystallized dianhydrohexitol.

In general, as applied to dianhydrogalactitol, this method comprises the steps of:

(1) converting dulcitol to dibromodulcitol by reaction of the dulcitol with hydrobromic acid for from about 12 hours to about 36 hours at an elevated temperature;

(2) adding the product of step (a) to water, agitating the product of step (1) added to water for from about 18 hours to about 36 hours, filtering the mixture of the product of step (1) and water, washing the mixture with a large volume of water, drying the solid product under nitrogen, and then subsequently washing the dried solid product with a large volume of an aliphatic ether;

(3) reacting the product of step (2) with an alkali metal salt of carbonate in a polar aprotic solvent at an elevated temperature;

(4) filtering the product of step (3) to remove the solids;

(5) washing the solids removed in step (4) with a polar aprotic solvent and combining the washings with the solids removed in step (4);

(6) concentrating the combination of the washings with the solids of step (5) to a volume that is approximately from about 0.20 to about 0.27 of the volume of polar aprotic solvent used in step (3) at a temperature of from about 30° C. to about 40° C.;

(7) agitating the concentrated product of step (6) for from about 18 hours to about 36 hours at a temperature of from about 0° C. to about 10° C.;

(8) washing the product of step (7) with an aliphatic ether;

(9) drying the washed product of step (8) under nitrogen; and

(10) recrystallizing the product of step (9) by:
(a) dissolving the product of step (9) in acetone;
(b) filtering off insoluble solids remaining after dissolving the product of step (9) in acetone;
(c) concentrating the solution of step (10)(a) down to a volume of about 0.07 to about 0.12 of the original volume of acetone;
(d) cooling the concentrated solution of step (10)(c) to about −20° C. to generate solid recrystallized dianhydrogalactitol and agitating the suspension of solid recrystallized dianhydrogalactitol for from about 18 hours to about 36 hours;
(e) filtering the solids of step (10)(d) and washing the solids with a large volume of an aliphatic ether; and
(f) drying the washed solids of step (10)(e) under nitrogen to produce solid recrystallized dianhydrogalactitol.

Typically, the elevated temperature of step (1) is from about 35° C. to about 45° C. Preferably, the elevated temperature of step (1) is about 40° C.

Typically, in step (1), the dulcitol is reacted with hydrobromic acid for from about 12 hours to about 24 hours. In some alternatives, the dulcitol can be reacted with hydrobromic acid for from about 12 hours to 18 hours.

Typically, the aliphatic ether of step (2) is selected from the group consisting of methyl t-butyl ether (MTBE), dimethyl ether, methyl ethyl ether, diethyl ether, dipropyl ether, methyl propyl ether, and ethyl propyl ether. Preferably, the aliphatic ether of step (2) is methyl t-butyl ether.

Typically, in step (2), the mixture of the product of step (1) added to water is agitated for about 24 hours.

Typically, the polar aprotic solvent of step (3) is tetrahydrofuran. Typically, the alkali metal salt of carbonate of step (3) is selected from the group consisting of lithium carbonate, sodium carbonate, and potassium carbonate. Preferably, the alkali metal salt of carbonate of step (3) is potassium carbonate. Typically, the elevated temperature of step (3) is from about 35° C. to about 45° C. Preferably, the elevated temperature of step (3) is about 40° C.

Typically, the temperature of step (6) is about 35° C.

Typically, the temperature of step (7) is about 4° C. Typically, in step (7), the concentrated product of step (6) is agitated for about 24 hours.

Typically, the aliphatic ether of step (8) is selected from the group consisting of methyl t-butyl ether, dimethyl ether, methyl ethyl ether, diethyl ether, dipropyl ether, methyl propyl ether, and ethyl propyl ether. Preferably, the aliphatic ether of step (8) is methyl t-butyl ether.

Typically, in step (10)(c), the solution of step (10)(a) is concentrated down to about 0.09 of the original volume of acetone. Typically, the agitation of step (10)(d) is performed for about 24 hours.

Typically, the aliphatic ether of step (10)(e) is selected from the group consisting of methyl t-butyl ether, dimethyl ether, methyl ethyl ether, diethyl ether, dipropyl ether, methyl propyl ether, and ethyl propyl ether. Preferably, the aliphatic ether of step (10)(e) is methyl t-butyl ether.

Typically, the drying of step (10)(f) is performed for a minimum of about 18 hours.

Typically, the recrystallized dianhydrogalactitol produced by the method described above, with steps (1)-(10), has total impurities of less than about 0.65%. Typically, the recrystallized dianhydrogalactitol produced by the method described above, with steps (1)-(10), has no detectable acetic acid, tetrahydrofuran, or methyl t-butyl ether. Typically, the recrystallized dianhydrogalactitol produced by the method described above, with steps (1)-(10), has residual acetone of less than about 0.2%. Typically, the recrystallized dianhydrogalactitol produced by the method described above, with steps (1)-(10), has a water content of less than about 2.2%.

Another aspect of the invention is purified recrystallized dianhydrogalactitol produced by the method described above, with steps (1)-(10). Typically, the purified recrystallized dianhydrogalactitol has total impurities of less than about 0.65%. Typically, the purified recrystallized dianhydrogalactitol has no detectable acetic acid, tetrahydrofuran, or methyl t-butyl ether. Typically, the purified recrystallized dianhydrogalactitol has residual acetone of less than about 0.2%. Typically, the purified recrystallized dianhydrogalactitol has a water content of less than about 2.2%.

Still another improvement on this process is particularly useful for further scaling up of the synthesis and producing dianhydrogalactitol or another substituted hexitol for pharmacological use with increased purity. In general, this alternative of the process comprises the steps of:

(1) converting a hexitol to a dibromo derivative of the hexitol by reaction of the hexitol with hydrobromic acid for from about 18 hours to about 24 hours at an elevated temperature, wherein the hydrobromic acid is at a concentration of from about 30% to about 35%, and wherein the elevated temperature is from about 35° C. to about 45° C.;

(2) precipitating the product of step (1) with water;

(3) washing the precipitated product of step (2) with an aliphatic ether;

(4) drying the washed product of step (3) under nitrogen and vacuum;

(5) converting the dibromo derivative of the hexitol from step (4) to the dianhydro derivative thereof by reacting with a base selected from the group consisting of potassium carbonate, N,N-diisopropylethylamine (DIPEA), triethanolamine (TEA), and 1,8-diazabicycloundec-7-ene (DBU) in a polar aprotic solvent at a temperature of from about 35° C. to 45° C. for from about 16 hours to about 20 hours;

(6) washing the product of step (5) with tetrahydrofuran and then with water; and (7) recrystallizing the product of step (6) from an aliphatic ketone to produce a dianhydro derivative of the hexitol.

In this process, the starting material (the hexitol) is preferably dulcitol. When the starting material is dulcitol, the dibromo derivative of the hexitol is dibromodulcitol and the dianhydro derivative of the hexitol is dianhydrogalactitol.

In this process, in step (1), the hydrobromic acid is preferably at a concentration of about 33%. In step (1), the elevated temperature is typically from about 37.5° C. to about 42.5° C. In step (1), the elevated temperature is preferably at about 40° C.

In this process, in step (3), typically the aliphatic ether is selected from the group consisting of methyl t-butyl ether, dimethyl ether, methyl ethyl ether, diethyl ether, dipropyl ether, methyl propyl ether, and ethyl propyl ether. Preferably, the aliphatic ether is methyl t-butyl ether.

In this process, in step (5), preferably the base is potassium carbonate.

In this process, in step (5), typically the polar aprotic solvent is selected from the group consisting of dimethylformamide and tetrahydrofuran. Preferably, the polar aprotic solvent is tetrahydrofuran.

In this process, in step (5), typically, the temperature is from about 37.5° C. to about 42.5° C. Preferably, the temperature is about 40° C.

In this process, in step (5), typically, the duration of the reaction is from about 17 hours to about 19 hours. Preferably, the duration of the reaction is about 18 hours.

In this process, in step (7), typically the aliphatic ketone is selected from the group consisting of diethyl ketone and acetone. Preferably, the aliphatic ketone is acetone.

When the product of the synthesis process is dianhydrogalactitol, typically the dianhydrogalactitol resulting from step (7) of the synthesis process is at a purity of at least 99.80%. Preferably, the dianhydrogalactitol is at a purity of about 99.91%. Typically, when the product of the synthesis process is dianhydrogalactitol, the dianhydrogalactitol contains less than 3500 ppm of the aliphatic ketone used for recrystallization in step (7), such as acetone. Preferably, when the product of the synthesis process is dianhydrogalactitol, the dianhydrogalactitol contains less than 3200 ppm of the aliphatic ketone used for recrystallization in step (7), such as acetone. Typically, when the product of the synthesis process is dianhydrogalactitol, the dianhydrogalactitol contains less than 90 ppm of the aliphatic ether used as a solvent in step (3), such as MTBE. Preferably, when the product of the synthesis process is dianhydrogalactitol, the dianhydrogalactitol contains less than 75 ppm of the aliphatic ether used as a solvent in step (3), such as MTBE. Preferably, when the product of the synthesis process is dianhydrogalactitol, the dianhydrogalactitol contains no detectable amount of the polar aprotic solvent used in step (5), such as THF.

Yet another aspect of the invention is a pharmaceutical composition comprising:

(1) a therapeutically effective quantity of the purified recrystallized dianhydrogalactitol prepared by the method described above (with steps (1)-(7)); and (2) at least one pharmaceutically acceptable carrier, diluent, or excipient.

BRIEF DESCRIPTION OF THE DRAWINGS

These and other features, aspects, and advantages of the present invention will become better understood with reference to the following description, appended claims, and accompanying drawings where:

DETAILED DESCRIPTION OF THE INVENTION

Figure 1:
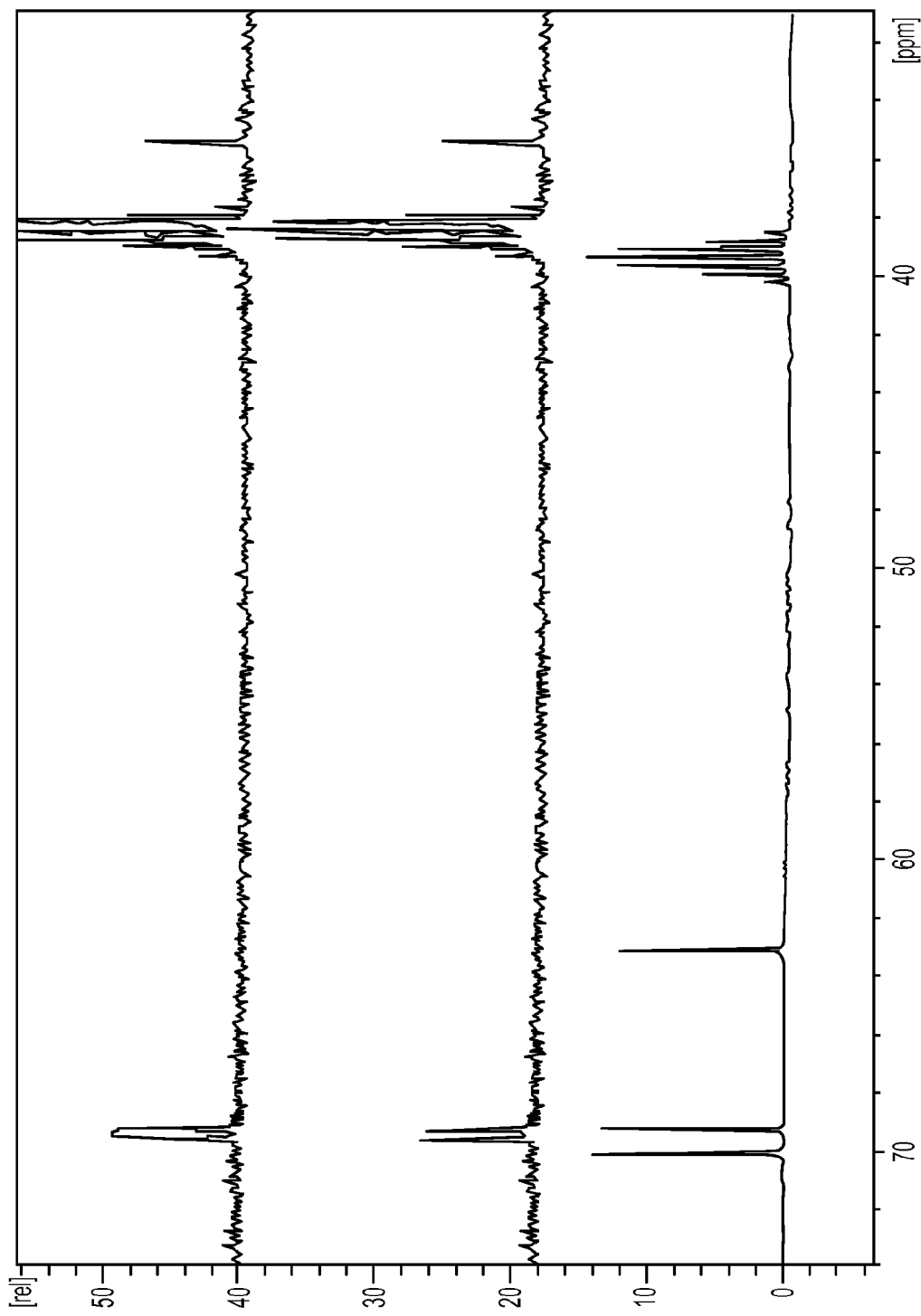
FIG. 1 shows disappearance of dulcitol at IPC #1 is shown by $^{13}$C-NMR in Example 1.

Dianhydrogalactitol (DAG) can be synthesized from dulcitol which can be produced from natural sources (such as *Maytenus confertiflora*) or commercial sources.

The structure of DAG is given below as Formula (I).

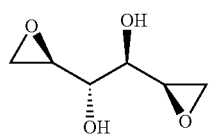

(I)

One method for the preparation of dulcitol from *Maytenus confertiflora* is as follows: (1) The *Maytenus confertiflora* plant is soaked in diluted ethanol (50-80%) for about 24 hours, and the soaking solution is collected. (2) The soaking step is repeated, and all soaking solutions are combined. (3) The solvent is removed by heating under reduced pressure. (4) The concentrated solution is allowed to settle overnight and the clear supernatant is collected. (5) Chloroform is used to extract the supernatant. The chloroform is then removed under heat and reduced pressure. (6) The residue is then dissolved in hot methanol and cooled to allow crystallization. (7) The collected crystals of dulcitol are filtered and dried under reduced pressure. The purified material is dulcitol, contained in the original *Maytenus confertiflora* plant at a concentration of about 0.1% (1/1000).

In one alternative, DAG can be prepared by two general synthetic routes as described below:

Route 1:

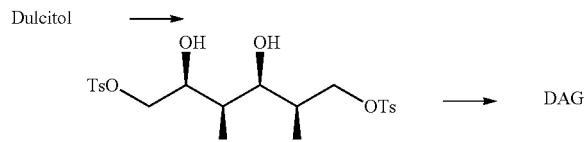

Route 2:

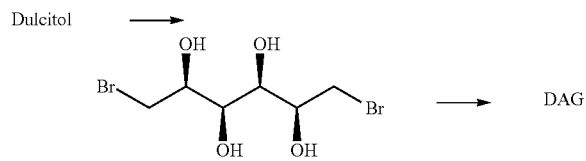

In Route 1, "Ts" represents the tosyl group, or p-toluenesulfonyl group.

However, the intermediate of Route 1, 1,6-ditosyldulcitol, was prepared with low yield (~36%), and the synthesis of 1,6-ditosyldulcitol was poorly reproducible. Therefore, the second route process was developed, involving two major steps: (1) preparation of dibromodulcitol from dulcitol; and (2) preparation of dianhydrodulcitol from dibromodulcitol.

Dibromodulcitol is prepared from dulcitol as follows: (1) With an aqueous HBr solution of approximately 45% HBr concentration, increase the HBr concentration to about 70% by reacting phosphorus with bromine in concentrated HBr in an autoclave. Cool the solution to 0° C. The reaction is: $2P+3Br_2 \rightarrow 2PBr_3+H_2O \rightarrow HBr\uparrow+H_3PO_4$. (2) Add the dulcitol to the concentrated HBr solution and reflux at 80° C. to complete the reaction. (3) Cool the solution and pour the mixture onto ice water. Dibromodulcitol is purified through recrystallization.

The results for the preparation of dibromodulcitol (DBD) are shown in Table 1, below.

TABLE 1

| Dulcitol | 18 g | 18 g | 18 g | 18 g |
|---|---|---|---|---|
| 45% aq. HBr | 36 mL | 36 mL | 36 mL | 36 mL |
| $PBr_3$ | 40 g | 40 g | 40 g | 40 g |
| Time | 7 h | 7 h | 7 h | 7 h |
| Temp/° C. | 70 | 70 | 70 | 70 |
| Crude Product | 25.2 g | 25.5 g | 24 g | 24.7 g |
| Yield | 84% | 85% | 80% | 82% |

For the preparation of DAG from DBD, DBD was poorly dissolved in methanol and ethanol at 40° C. (different from what was described in U.S. Pat. No. 3,993,781 to Horvath nee Lengyel et al., incorporated herein by this reference). At refluxing, DBD was dissolved but TLC showed that new impurities formed that were difficult to remove from DBD.

The DBD was reacted with potassium carbonate to convert the DBD to dianhydrogalactitol.

The results are shown in Table 2, below.

TABLE 2

| DBD | 0.5 g | 5 g | 4.3 g |
|---|---|---|---|
| $K_2CO_3$ | 1 g | 8 g | 4 g |
| t-BuOH | 5 mL | 50 mL | 40 mL |
| DAG | 0.17 g | 1 g | 0.82 g |
| Yield | 72% | 42% | 40% |

In the scale-up development, it was found the crude yield dropped significantly. It is unclear if DAG could be azeotropic with BuOH. It was confirmed that t-BuOH is essential to the reaction. Using MeOH as solvent would result in many impurities as shown spots on TLC. However, an improved purification method was developed by using a slurry with ethyl ether, which could provide DAG with good purity. This was developed after a number of failed attempts at recrystallization of DAG.

Accordingly, one aspect of the present invention is a method for synthesizing and purifying dianhydrogalactitol (DAG) comprising the steps of:

(1) reacting dulcitol with a concentrated solution of hydrobromic acid at a temperature of about 80° C. to produce dibromogalactitol;

(2) reacting the dibromogalactitol with potassium carbonate in t-butanol to produce dianhydrogalactitol; and (3) purifying the dianhydrogalactitol using a slurry of ethyl ether to produce purified dianhydrogalactitol.

In this method, typically, the concentrated solution of hydrobromic acid is about 70% hydrobromic acid and is produced by reacting phosphorus with bromine in hydrobromic acid at elevated temperature. Typically, the dibromogalactitol is dissolved in t-butanol in a proportion of about 1 g of dibromogalactitol to 10 mL of t-butanol. Typically, the dibromogalactitol is purified by recrystallization prior to its conversion to dianhydrogalactitol.

In this method, typically, the dulcitol is purified from the plant *Maytenus confertiflora* by the steps of:

(a) soaking the plant *Maytenus confertiflora* in a soaking solution of from about 50% to about 80% of ethanol for about 24 hours;

(b) collecting the soaking solution from step (a);

(c) repeating the soaking step of step (a) with a fresh soaking solution of from about 50% to about 80% of ethanol for about 24 hours;

(d) collecting the soaking solution from step (c) and combining it with the soaking solution collected in step (b);

(e) removing the solvent from the combined soaking solutions of step (iv) by heating under reduced pressure to produce a concentrated solution;
(f) allowing the concentrated solution of step (e) to settle overnight and collecting the clear supernatant;
(g) extracting the clear supernatant from step (f) with chloroform and then removing the chloroform under heat and reduced pressure;
(h) dissolving the residue from step (g) in hot methanol and then cooling to allow crystallization; and
(i) collecting the collected crystals of dulcitol, filtering, and drying the crystals under reduced pressure.

Another embodiment of the invention is a method for synthesizing and purifying a dianhydrohexitol comprising the steps of:
(1) reacting a hexitol bearing two epoxide groups with a concentrated solution of hydrobromic acid at a temperature of about 80° C. to produce a dibromohexitol;
(2) reacting the dibromohexitol with an alkali metal salt of carbonate in a tertiary alcohol to produce a dianhydrohexitol; and
(3) purifying the dianhydrohexitol using a slurry of an ether to produce the purified dianhydrohexitol.

In this method, the dianhydrohexitol can be, for example, dianhydrogalactitol or another dianhydrohexitol that has two epoxide groups, such as a substituted dianhydrogalactitol, as described above. However, typically the dianhydrohexitol is dianhydrogalactitol.

In this method, the alkali metal salt of carbonate is typically selected from the group consisting of sodium carbonate and potassium carbonate. Preferably, the alkali metal salt of carbonate is potassium carbonate ($K_2CO_3$).

In this method, the tertiary alcohol is typically t-butanol; however, other tertiary alcohols can be alternatively employed. Such tertiary alcohols include, for example, 2-methyl-2-butanol, 3-ethylpentanol, and other tertiary alcohols, typically containing 6 carbons or fewer.

In this method, the debromination step (step (2) above) occurs under refluxing conditions, which means that, when the tertiary alcohol is t-butanol, which has a boiling point of 82° C., reflux temperature would be about 80-85° C.

In this method, in the step of purifying the dianhydrohexitol from the ether slurry (step (3) above), the ether is typically an aliphatic ether with lower alkyl groups, such as dimethyl ether, methyl ethyl ether, diethyl ether, dipropyl ether, methyl propyl ether, and ethyl propyl ether. However, a preferable ether is diethyl ether.

Additional alternatives for the synthesis of dianhydrogalactitol are described. In general, in these alternatives, dianhydrogalactitol synthesis involves three major steps: (1) preparation of dibromodulcitol (DBD) from a commercial source of dulcitol; (2) preparation of dianhydrogalactitol (DAG) from DBD; and (3) recrystallization to purify the DAG.

The specific process for each step is described below:
For the preparation of DBD, the reaction is as shown in Scheme 1 (Step 1), below:

Scheme 1 (Step 1)

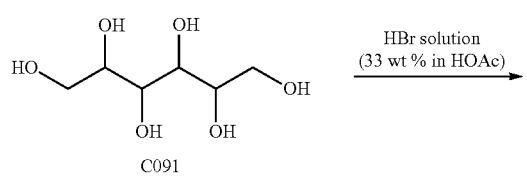

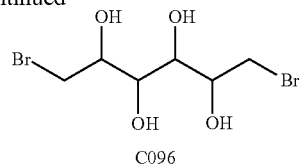

Hydrobromic acid (33% HBr in acetic acid, 2.1 eq) was added to 50 g of dulcitol (1 eq) and mixed. The mixture was then heated to 40° C. and mixed for 18 hours yielding a turbid suspension. The suspension was cooled to room temperature. Water (2 parts) was added and mixed for 18-24 hours and then filtered through a Buchner funnel. The collected solid was washed with water (4 parts) and dried under vacuum and nitrogen for 2 days to obtain off-white to light brown solid (DBD), 34 g or about 40% yield.

This method can be modified according by the use of alternatives known to those of ordinary skill in the art. For example, a relatively low-molecular-weight monoprotic acid such as formic acid or propanoic acid can replace acetic acid.

For the preparation of dianhydrogalactitol from dibromodulcitol, the reaction is as shown in Scheme 2 (Step 2).

Scheme 2 (Step 2)

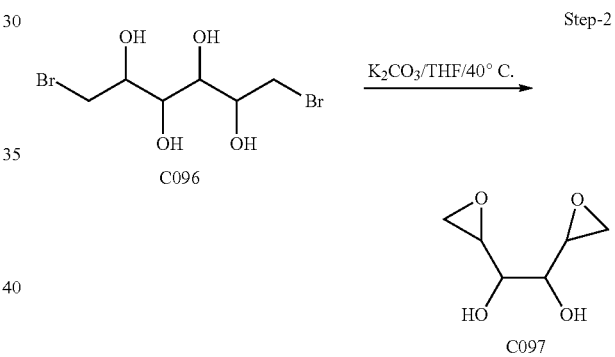

In this method 56 g (2.5 eq) potassium carbonate and THF (tetrahydrofuran) (15 parts) were added to 50 g of DBD (1 eq) and mixed. The mixture was heated to 40° C. and mixed for 18 hours and then cooled to room temperature. The product was filtered through Buchner funnel to remove inorganic solid and washed twice with THF. The filtrate and washes were collected and concentrated to 4-5 parts with water bath set at 35° C. Heptane (10 parts) was added and mixed for 1-2 hours at room temperature. The mixture was filtered through a Buchner funnel and washed twice with heptane. The solid was dried under vacuum and nitrogen for 18-24 hours at room temperature to obtain 19 g crude DAG, about 80% yield.

The final step is recrystallization of DAG. THF (20 parts) was added to 18.5 g of crude DAG (1 eq) and mixed for 1-2 hours at room temperature. The mixture was filtered through a Buchner funnel to discard solid. Heptane (20 parts) was slowly added and mixed for 2-4 hours at room temperature. The mixture was filtered. The solid was dried under vacuum and nitrogen for 18-24 hours at room temperature to obtain 10 g crude DAG, about 54% yield.

In this method, other nonpolar organic solvents, typically saturated hydrocarbons such as hexane or octane, can be used in place of heptane. In this methods, other relatively polar but aprotic organic solvents can be used in place of tetrahydrofuran.

Other alternative methods for preparation of DAG are described below. 1,2:5,6-dianhydrodulcitol (also known as DAG) is a compound with multiple hydroxyl groups and epoxide groups. This characteristic structure determines instability of this compound because of the tendency of the epoxide ring to open under acid, base or heat conditions. These methods start with dulcitol rather than dibromodulcitol.

In one additional alternative, the 1,6-hydroxy groups on dulcitol (available commercially) are modified to convert to an effective leaving group such as Br, OTf (triflate or trifluoromethane sulfonate), or OTs (tosylate), and then, using an inorganic weak base, the target compound DAG is prepared through an intramolecular $S_N 2$ reaction as shown in Scheme 3.

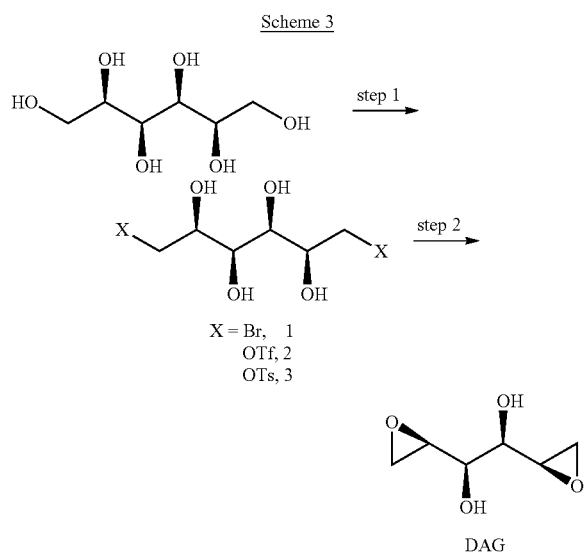

In this alternative, a preferred leaving group is Br. For Step 1 as shown in Scheme 3, there are four possible methods to prepare the intermediate with four hydroxyl groups and two leaving groups (e.g., Br). These methods are as follows when Br is to be introduced as the leaving group. This intermediate is designated Compound 1a below:

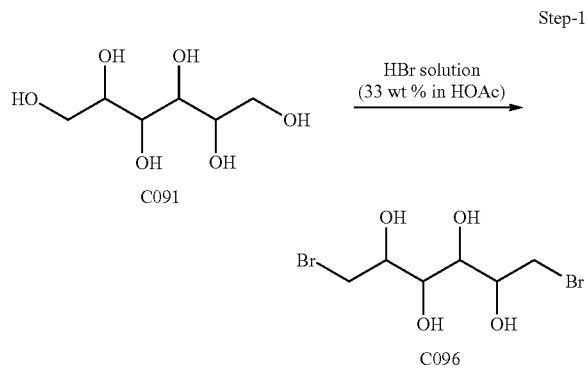

Method A for Preparation of Intermediate

The conditions are 45-48% HBr aq/P/Br$_2$/70° C., 5-7 hr. The procedure is as follows: Add phosphorus to aqueous solution of 45-48% HBr at 0° C. and carefully add Br$_2$ dropwise to make HBr solution with concentration about 60-70%. Add dulcitol and heat to 70° C. in a closed reactor for 5-7 hours. After the completion of reaction, cool the reaction mass to room temperature and pour into ice water to obtain the crude compound 1a (the intermediate referred to above with four hydroxyl groups and two leaving groups (e.g., Br)). For purification, a polar solvent without a nucleophilic property, such as 2-chloromethane/t-butanol or 2-chloromethane/isopropyl alcohol is used for recrystallization. Due to the instability of compound 1a (the intermediate referred to above) (hydrolysis under D$_2$O/room temp or H$_2$O/reverse) so that it is reconverted back to dulcitol, it is important to avoid hydrolysis so that Compound 1a is not converted back to dulcitol in the course of recrystallization or column chromatography.

This method has high yield (~80%) with good repeatability. However, it requires the use of corrosive HBr solution and volatile, toxic Br$_2$.

Method B for Preparation of Intermediate

The conditions are 62% HBr aq/P/Br$_2$/70° C., 5-7 hr. The procedure is as follows: Add dulcitol to 62% HBr aqueous solution. Heat to 70° C. in a closed reactor for 5-7 hours. After the completion of reaction, cool the reaction mass to room temperature and pour into ice water to obtain the crude Compound 1a. For purification, use mixed solvents of 2-chloromethane/t-butanol or 2-chloromethane/isopropyl alcohol for recrystallization.

This method uses commercial 62% HBr aqueous solution to simplify the procedures and avoid high risk using Br$_2$. However, the reaction needs highly corrosive HBr solution and volatile, toxic Br$_2$.

Method C for Preparation of Intermediate

The conditions are 33% HBr in HOAc/r.t., 5-7 hr. The procedure is as follows: Add dulcitol to 33% HBr solution in acetic acid, mix for 5-7 hours at room temperature. Add methanol and mix for 15 hours. Concentrate under vacuum to remove most of the solvent. Pour the remaining solution into ice water to collect the crude Compound 1a. For purification, use mixed solvents of 2-chloromethane/t-butanol or 2-chloromethane/isopropyl alcohol for recrystallization.

This alternative uses commercial 33% HBr acetic solution with simple procedures. However, the reaction requires use of highly corrosive HBr solution.

Method D for Preparation of Intermediate

The conditions are: CBr$_4$/Ph$_3$P/pyridine or DMF/r.t., 15-18 hr. The procedure is as follows: Dissolve dulcitol in pyridine or dimethylformamide (DMF) at room temperature. Add CBr$_4$ and Ph$_3$P in sequence and mix for 15-18 hours at room temperature. After the completion of reaction, concentrate under vacuum to remove solvent and chloroform formed from reaction. Wash the remaining solid several times with dichloromethane to remove triphenylphosphine byproduct. For purification, use mixed solvents of 2-chloromethane/t-butanol or 2-chloromethane/isopropyl alcohol for recrystallization.

The advantages of this method are moderate reaction conditions without using HBr or Br$_2$. However, the reaction will produce triphenylphosphine byproduct which will affect the purity of Compound 1a (the intermediate referred to above with four hydroxyl groups and two leaving groups (e.g., Br).

As indicated above, the 1,6-hydroxy groups can be modified by other leaving groups, such as TfO— (Compound 1 b) or TsO— (Compound 1c) in Step 1. Since there are several hydroxyl groups in dulcitol, it is important to control the reagent quantity during sulfonylation reaction.

For the preparation of Compound 1 b or Compound 1c, the conditions are: TsCl or Tf$_2$O/Pyridine/0° C., 4-8 hr. The procedure is as follows: Dissolve dulcitol in pyridine. Add TsCl or Tf$_2$O at 0° C. and mix for 15-18 hours. After the completion of reaction, concentrate under vacuum to remove solvent. Pour the remaining solution into ice water to obtain crude Compound 1 b or Compound 1c as referred to above (i.e, the compounds with modified leaving groups). For purification, use mixed solvents of 2-chloromethane/t-butanol or 2-chloromethane/isopropyl alcohol for recrystallization.

Typically, this method generates an equivalent of the pyridine salt of p-toluenesulfonic acid or trifluoromethanesulfonic acid. Removal of these byproducts is important in yielding Compound 1b or Compound 1c in high purity.

For Step 2 of this procedure, resulting in DAG, one alternative, described above, uses conditions of K$_2$CO$_3$/t-BuOH. However, this may not be optimum in larger-scale preparations. Under small scale conditions (0.5 g), moderate yield (~70%) can be achieved. The yield was significantly reduced to ~40% when the scale was 4 g. Although Applicant does not intend to be bound by this supposition, this may result from the formation of an azeotropic mixture of DAG and t-butanol with a low boiling point. Therefore, as indicated above, this may not be efficiently scalable for preparations >1 g.

Under alkaline conditions, Compound 1a, 1b, or 1c, described above (the intermediate prior to the formation of DAG) may undergo a series of side reactions shown in Scheme 4.

reaction to produce DAG as target product. The inorganic alkali used is not nucleophilic and does not cause intermolecular nucleophilic substitution. The polar nonionic solvent not only provides better solubility for inorganic alkali and a more polar alcohol reactant 1a, 1b, or 1c, but also will not cause side reactions because of the lack of nucleophilicity. In addition, replacing the reported t-butanol with this solvent, the co-distillation (azeotrope formation) between DAG and t-butanol can be avoided. This will resolve the scale-up issue. The specific conditions are as follows: K$_2$CO$_3$/DMF/r.t., 5-7 hr. The procedure is as follows: Dissolve the product from Step 1 (i.e., Compound 1a, Compound 1 b, or Compound 1c), in a polar nonionic solvent such as DMF. Add K$_2$CO$_3$ or the other inorganic carbonate and mix at room temperature for 5-7 hours. After completion of the reaction, add p-toluenesulfonic acid to neutralize potassium carbonate or other inorganic carbonate. Concentrate under vacuum to remove solvent. Wash the remaining solid with water to remove the inorganic impurities. For purification, add ether to crude material and mix vigorously. Filter the slurry to obtain target DAG.

In another alternative, the synthetic route for dianhydrogalactitol is as shown in Scheme 5.

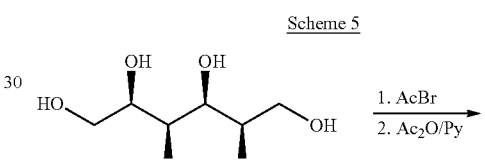

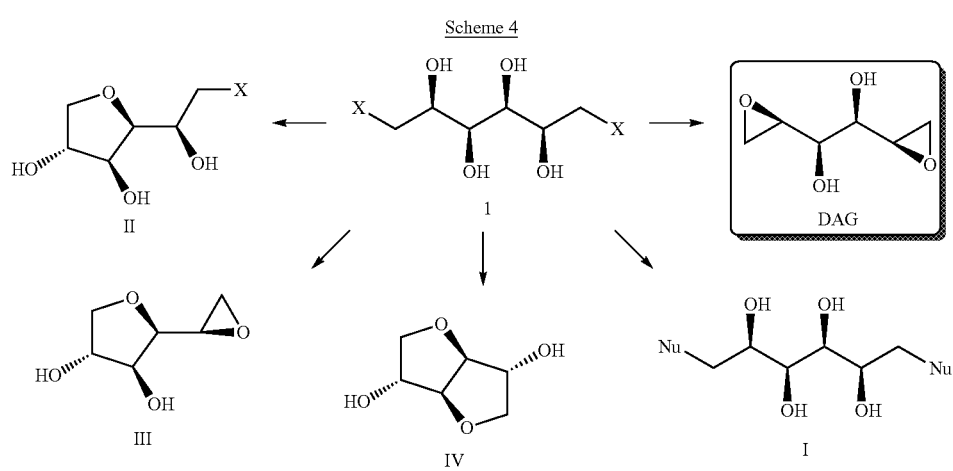

These side reactions may include intermolecular reactions due to nucleophilic reagent of alkaline or solvent (alcohol or water) to produce side product I; or intra-molecular attack by hydroxyl group to produce byproducts (I-IV) with a furan ring, formed more rapidly compared to epoxide. Therefore, it is critical to select or control the step 2 reaction conditions to prevent the occurrence of side reactions to the extent possible.

In this alternative, it is generally preferred to use an inorganic alkali (such as K$_2$CO$_3$, Cs$_2$CO$_3$, or other inorganic carbonates) and a polar nonionic solvent favorable for S$_N$2

-continued

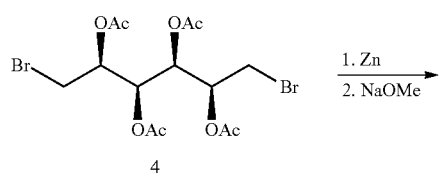

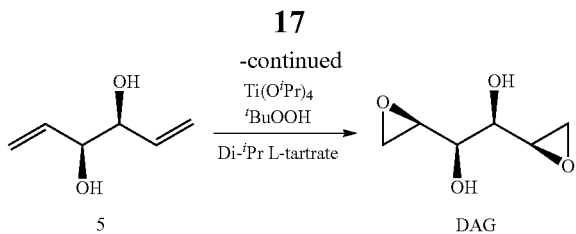

In the synthetic route of Scheme 5, the process starts with substitution of 1,6 hydroxy groups with bromine and other hydroxyl groups with acetyl groups yielding compound 4, which is then reacted with zinc to form double bonds through an elimination reaction with a molecular conjugated base such as sodium methoxide. The protective acetyl group is removed to yield compound 5. Finally, through the use of the Sharpless epoxidation reaction, the target compound DAG is formed. Typically, the substitution of the 1,6 hydroxy groups is performed with reaction with acetyl bromide; alternatively, other bromide-substituted acyl compounds can be used. Typically, the acetylation of the hydroxy groups other than the 1,6-hydroxy groups is performed with acetic anhydride in pyridine.

Another embodiment of the invention provides recrystallized dianhydrogalactitol in a four-stage process. This four-stage process begins with dibromodulcitol. This four-stage process produces high-purity dianhydrogalactitol and can be scaled up for the production of large quantities of high-purity recrystallized dianhydrogalactitol. This embodiment has a number of advantages. It utilizes commercially available hydrobromic acid in acetic acid at a concentration of 33% to 48% to allow reaction with dulcitol to proceed at ambient room temperature or at an elevated temperature up to 50° C. This avoids the necessity of using high concentrations of hydrobromic acid (>56%) under high temperature and high pressure, which requires handling of a concentrated hydrobromic acid solution that is hazardous and very corrosive to piping and reactors. The use of such a concentrated hydrobromic acid solution requires use of a specially designed reactor that is protected from corrosive hydrobromic acid. Such a reactor is expensive and the requirement for its use makes the process less flexible for changing the scale of the synthesis. This embodiment avoids the requirement for replacement of a specialized cation exchange resin which is available from limited suppliers and requires pretreatment before use; in addition, special equipment and procedures are required for washing the cation exchange resin with sodium hydroxide. This is avoided by use of this embodiment. The new process described in this embodiment is easy to scale up with flexibility of batch size and lower manufacturing cost. This embodiment is described below in terms of a 100-g batch; it has already been scaled up to a 200-g batch with purity of >99.0%. Details of this embodiment are provided below.

The first stage of this process is directed to the conversion of dulcitol to dibromodulcitol. In the first stage of this four-stage process, a 20-liter reactor is used with the outlet connected to a trap flask containing 1 N NaOH solution. Hydrobromic acid solution (33%) is charged at room temperature in one portion (9.7 liters, 2.1 equivalents, 2.02 parts). Dulcitol (4.8 kg, 26.35 mol, 1.0 equivalents) is charged slowly in small portions through the manway of the reactor with agitation. The reaction mixture is heated to 40° C. and then agitated for 18-24 hours at 40° C. The reaction mixture is cooled to room temperature to yield an off-white suspension. An 0.5 mL sample is taken for in-process analysis; the dulcitol content by HPLC is to be limited to <0.02%. In this stage, HBr vapors are present during the charging of the hydrobromic acid solution. Care should be taken to minimize contact with air during charging. Any plastic parts on the reactor will degrade on contact with the HBr vapors. HBr vapors will also be present during the charging with the solid dulcitol. Care should be taken to minimize escape of these vapors during the charging with the solid dulcitol.

The second stage is a work-up of the dibromodulcitol. In this stage, D.I. water is charged at ambient temperature (9.6 liters, 2 parts) in about 30 minutes. The mixture is agitated at ambient temperature for 24 hours (white solid suspension). The reaction mixture is filtered and the solids are washed with 2×5 L of D. I. water. The solids are dried at ambient temperature under nitrogen for 12 hours. Suction is applied to the filter to increase nitrogen flow through the solid. The solids are washed with 2×4 L of methyl t-butyl ether (MTBE). The solids are dried at ambient temperature under nitrogen for 48-72 hours. Suction is applied to the filter to increase nitrogen flow through the solid. The yield is 3.2 kg dibromodulcitol (38%). Characterization testing results are: total impurities, 10.8%; residual HOAc (acetic acid), 0.67%; water content, 2.14%.

The third stage is the conversion of dibromodulcitol (DBD) to crude dianhydrogalactitol (DAG). In the third stage, a nitrogen-purged 1-liter three-neck round bottom flask is used. The round-bottom flask is equipped with a magnetic stirrer, nitrogen thermometer, and condenser. DBD (50 g, 0.162 mol, 1.0 equivalents) is charged to the reaction flask. Potassium carbonate (56 g, 0.405 mol, 2.5 equivalents) is then charged to the reaction flask. Tetrahydrofuran (THF) (750 mL, 15 parts) is then charged into the reaction flask and agitation of the white suspension is started. Heating of the reaction mixture is then begun and the temperature is adjusted to 40° C. The reaction mixture is maintained at 40° C. for 18 hours and then cooled to ambient temperature. An 0.5 mL sample is taken for in-process analysis; the DAG content is assessed by HPLC (limit: >30%). The reaction mixture is then filtered to remove the inorganic solids. The inorganic solids are washed using 2×125 mL (2.5 parts) of THF. Then, the THF washes are combined with the filtrate and concentrated down to about 150-200 mL (3-4 parts) with bath temperature set at 35° C. The resulting suspension is then cooled to 4° C. The white suspension is then agitated for 24 hours at 4° C. The solids are then filtered and washed with 100 mL (2 parts) MTBE. The white solids are then dried at ambient temperature under nitrogen for a minimum of 18 hours. Suction is applied to the filter to increase nitrogen flow through the solid. The yield is 13.7 g crude DAG (68%). Characterization testing results are: total impurities, 1.44%; residual HOAc/MTBE, not detectable; residual THF, 0.23%.

The fourth stage is the recrystallization of the DAG. In the fourth stage, a nitrogen-purged 1-liter three-neck round bottom flask is used. The round-bottom flask is equipped with a magnetic stirrer, nitrogen thermometer, and condenser. Crude DAG (11 g) is charged into the reaction flask at room temperature. Acetone (275 mL, 25 parts) is charged into a reaction flask at ambient temperature and agitation is started. The reaction mixture, which is slightly cloudy, is agitated at ambient temperature for 30 minutes. The insoluble solids are filtered off and the acetone filtrate is collected. The acetone filtrate is then charged back to the reaction flask and concentrated down to about 25 mL (about 2 parts) with the bath temperature set at 30° C. The reaction mixture is then cooled to −20° C. and then agitated for 24 hours at −20° C.; the reaction mixture is a white suspension.

The solids are filtered and washed with 44 mL (4 parts) MTBE. The solids are dried at ambient temperature under nitrogen for a minimum of 18 hours. Suction is applied to the filter to increase nitrogen flow through the solid. 10 g white solid of DAG is yielded (91%). Characterization testing results are: total impurities, 0.63%; residual HOAc/THF/MTBE, not detectable; residual acetone: 0.14%; water content, 2.14%.

This method is suitable for scaling up and for the production of large quantities of recrystallized dianhydrogalactitol. This method can be applied to other hexitols.

In general, as applied to the synthesis of a dianhydrohexitol, the method comprises the steps of:

(1) converting a hexitol to a dibromo derivative of the hexitol by reaction of the dulcitol with hydrobromic acid for from about 12 hours to about 36 hours at an elevated temperature;

(2) adding the product of step (1) to water, agitating the product of step (1) added to water for from about 18 hours to about 36 hours, filtering the mixture of the product of step (1) and water, washing the mixture with a large volume of water, drying the solid product under nitrogen, and then subsequently washing the dried solid product with a large volume of an aliphatic ether;

(3) reacting the product of step (b) with an alkali metal salt of carbonate in a polar aprotic solvent at an elevated temperature;

(4) filtering the product of step (3) to remove the solids;

(5) washing the solids removed in step (4) with a polar aprotic solvent and combining the washings with the solids removed in step (4);

(6) concentrating the combination of the washings with the solids of step (5) to a volume that is approximately from about 0.20 to about 0.27 of the volume of polar aprotic solvent used in step (3) at a temperature of from about 30° C. to about 40° C.;

(7) agitating the concentrated product of step (6) for from about 18 hours to about 36 hours at a temperature of from about 0° C. to about 10° C.;

(8) washing the product of step (7) with an aliphatic ether;

(9) drying the washed product of step (8) under nitrogen; and

(10) recrystallizing the product of step (9) by:
(a) dissolving the product of step (9) in acetone;
(b) filtering off insoluble solids remaining after dissolving the product of step (9) in acetone;
(c) concentrating the solution of step (10)(a) down to a volume of about 0.07 to about 0.12 of the original volume of acetone;
(d) cooling the concentrated solution of step (10)(c) to about −20° C. to generate solid recrystallized dianhydrohexitol and agitating the suspension of solid recrystallized dianhydrohexitol for from about 18 hours to about 36 hours;
(e) filtering the solids of step (10)(d) and washing the solids with a large volume of an aliphatic ether; and
(f) drying the washed solids of step (10)(e) under nitrogen to produce a solid recrystallized dianhydrohexitol.

Accordingly, a method for synthesizing and recrystallizing dianhydrogalactitol that is suitable for large-scale preparation of purified dianhydrogalactitol comprises the steps of:

(1) converting dulcitol to dibromodulcitol by reaction of the dulcitol with hydrobromic acid for from about 12 hours to about 36 hours at an elevated temperature;

(2) adding the product of step (a) to water, agitating the product of step (1) added to water for from about 18 hours to about 36 hours, filtering the mixture of the product of step (1) and water, washing the mixture with a large volume of water, drying the solid product under nitrogen, and then subsequently washing the dried solid product with a large volume of an aliphatic ether;

(3) reacting the product of step (2) with an alkali metal salt of carbonate in a polar aprotic solvent at an elevated temperature;

(4) filtering the product of step (3) to remove the solids;

(5) washing the solids removed in step (4) with a polar aprotic solvent and combining the washings with the solids removed in step (4);

(6) concentrating the combination of the washings with the solids of step (5) to a volume that is approximately from about 0.20 to about 0.27 of the volume of polar aprotic solvent used in step (3) at a temperature of from about 30° C. to about 40° C.;

(7) agitating the concentrated product of step (6) for from about 18 hours to about 36 hours at a temperature of from about 0° C. to about 10° C.;

(8) washing the product of step (7) with an aliphatic ether;

(9) drying the washed product of step (8) under nitrogen; and

(10) recrystallizing the product of step (9) by:
(a) dissolving the product of step (9) in acetone;
(b) filtering off insoluble solids remaining after dissolving the product of step (9) in acetone;
(c) concentrating the solution of step (10)(a) down to a volume of about 0.07 to about 0.12 of the original volume of acetone;
(d) cooling the concentrated solution of step (10)(c) to about −20° C. to generate solid recrystallized dianhydrogalactitol and agitating the suspension of solid recrystallized dianhydrogalactitol for from about 18 hours to about 36 hours;
(e) filtering the solids of step (10)(d) and washing the solids with a large volume of an aliphatic ether; and
(f) drying the washed solids of step (10)(e) under nitrogen to produce solid recrystallized dianhydrogalactitol.

Typically, the elevated temperature of step (1) is from about 35° C. to about 45° C. Preferably, the elevated temperature of step (1) is about 40° C.

Typically, in step (1), the dulcitol is reacted with hydrobromic acid from about 18 hours to about 24 hours.

Typically, the aliphatic ether of step (2) is selected from the group consisting of methyl t-butyl ether, dimethyl ether, methyl ethyl ether, diethyl ether, dipropyl ether, methyl propyl ether, and ethyl propyl ether. Preferably, the aliphatic ether of step (2) is methyl t-butyl ether.

Typically, in step (2), the mixture of the product of step (1) added to water is agitated for about 24 hours.

Typically, the polar aprotic solvent of step (3) is tetrahydrofuran. Typically, the alkali metal salt of carbonate of step (3) is selected from the group consisting of lithium carbonate, sodium carbonate, and potassium carbonate. Preferably, the alkali metal salt of carbonate of step (3) is potassium carbonate. Typically, the elevated temperature of step (3) is from about 35° C. to about 45° C. Preferably, the elevated temperature of step (3) is about 40° C.

Typically, the temperature of step (6) is about 35° C.

Typically, the temperature of step (7) is about 4° C. Typically, in step (7), the concentrated product of step (6) is agitated for about 24 hours.

Typically, the aliphatic ether of step (8) is selected from the group consisting of methyl t-butyl ether, dimethyl ether, methyl ethyl ether, diethyl ether, dipropyl ether, methyl propyl ether, and ethyl propyl ether. Preferably, the aliphatic ether of step (8) is methyl t-butyl ether.

Typically, in step (10)(c), the solution of step (10)(a) is concentrated down to about 0.09 of the original volume of acetone. Typically, the agitation of step (10)(d) is performed for about 24 hours.

Typically, the aliphatic ether of step (10)(e) is selected from the group consisting of methyl t-butyl ether, dimethyl ether, methyl ethyl ether, diethyl ether, dipropyl ether, methyl propyl ether, and ethyl propyl ether. Preferably, the aliphatic ether of step (10)(e) is methyl t-butyl ether (MTBE).

Typically, the drying of step (10)(f) is performed for a minimum of about 18 hours.

Typically, the recrystallized dianhydrogalactitol produced by the method described above, with steps (1)-(10), has total impurities of less than about 0.65%. Typically, the recrystallized dianhydrogalactitol produced by the method described above, with steps (1)-(10), has no detectable acetic acid, tetrahydrofuran, or methyl t-butyl ether. Typically, the recrystallized dianhydrogalactitol produced by the method described above, with steps (1)-(10), has residual acetone of less than about 0.15%. Typically, the recrystallized dianhydrogalactitol produced by the method described above, with steps (1)-(10), has a water content of less than about 2.15%.

Another aspect of the invention is purified recrystallized dianhydrogalactitol produced by the method described above, with steps (1)-(10). Typically, the purified recrystallized dianhydrogalactitol has total impurities of less than about 0.65%. Typically, the purified recrystallized dianhydrogalactitol has no detectable acetic acid, tetrahydrofuran, or methyl t-butyl ether. Typically, the purified recrystallized dianhydrogalactitol has residual acetone of less than about 0.15%. Typically, the purified recrystallized dianhydrogalactitol has a water content of less than about 2.15%.

A further refinement of this process is described below. This refinement of the process provides efficient synthesis and purification of substituted hexitols such as dianhydrogalactitol in the larger quantities needed for the preparation of therapeutically active drugs and pharmaceutical compositions. This refinement of the process is even more scalable and efficient for the production of such substituted hexitols in larger quantities as required for clinical use.

This refinement of this process represents a further scale-up of the four-step process described above: ((i) conversion of dulcitol to dibromodulcitol; (ii) work-up and partial purification of dibromodulcitol; (iii) conversion of dibromodulcitol to dianhydrogalactitol; and (iv) recrystallization of dianhydrogalactitol.

For the first step of the refinement of the process (step (i), conversion of dulcitol to dibromodulcitol), the first step can be performed as follows. The reaction vessel is a 20-liter reactor with the outlet connected to a trap flask containing 1N NaOH solution. Hydrobromic acid solution (33%) is charged to the reactor at room temperature in one portion (9.7 L, 2.1 equivalents, 2.02 parts). Dulcitol (4.8 kg, 26.35 mol, 1.0 equivalents) was charged slowly in small portions through the manway with agitation. Excessively rapid charging results in the formation of a solid mass. The reaction mixture is then heated to 40° C. and agitated for 18 to 24 hours at 40° C. The reaction mixture is then cooled to room temperature to yield an off-white suspension. An 0.5-mL sample is then withdrawn for in-process analysis. The dulcitol content is <0.02% by HPLC.

The original process involved preparing 70% HBr in a pressure reactor and heating to 90° C. However, this process involves high temperatures and high concentrations of hydrobromic acid and is difficult to scale up to the desired volumes. The use of 48% HBr aqueous solution with heating at 80° C. for 18 hours did not yield detectable dibromodulcitol product. Similarly, the use of 33% HBr in acetic acid with heating at 90° C. for 18 hours did not yield detectable dibromodulcitol product.

For the second step of the process (step (ii), work-up and partial purification of dibromodulcitol), the reactor was charged with deionized water at ambient temperature (9.6 L, 2 parts) in about 30 minutes. The product from step (i) and the water were agitated at ambient temperature for 24 hours; a white solid suspension was formed. The reaction mixture was filtered and the solids washed with 2×5 L of deionized water. The solids were dried at ambient temperature under nitrogen for 12 hours. Suction was applied to the filter to increase nitrogen flow through the solid material. The solids were washed with 2×4 L of methyl t-butyl ether (MTBE). The solids were dried at ambient temperature under nitrogen and vacuum for 48-72 hours. The yield was 3.2% kg of dibromodulcitol (38%).

Different isolation methods have been tried to quench the reaction after DBD formation. Alternatives to water in the initial quenching step include MTBE, toluene, and acetic acid. However, water is preferred for the initial quenching step after DBD formation.

For the third step of the process (step (iii), conversion of dibromodulcitol to dianhydrogalactitol), the reaction vessel is a nitrogen-purged 12-L three-neck round-bottom flask equipped with a magnetic stirrer, nitrogen thermometer, and condenser. Dibromodulcitol (720 g, 2.34 mol, 1.0 equivalents) and tetrahydrofuran (THF) (10.8 L, 5 parts) is charged to the reaction flask. Agitation is started. Potassium carbonate ($K_2CO_3$) (808 g, 5.85 mol, 2.5 equivalents) was slowly charged to the reaction flask. Heating of the reaction mixture was begun and the temperature of the reaction mixture was adjusted to 40° C. The reaction temperature was maintained at 40° C. for 18 hours. The reaction mixture was then cooled to ambient temperature. An 0.5-mL sample was withdrawn for in-process analysis. Dianhydrogalactitol (DAG) content was analyzed by HPLC. The acceptable content of DAG was >30%. The reaction mixture was filtered to remove the inorganic solids. The inorganic solids were washed using 2×125 mL (2.5 parts) of tetrahydrofuran (THF). All the THF washes were combined with the filtrate and concentrated down to 1.5-2.5 parts under vacuum with the jacket temperature set to 35° C. The resulting suspension is cooled to 0° C. over 4 hours and the white suspension is agitated for 18 hours at 0° C. The solids are then filtered and washed with 2×1 parts of MTBE. This yields crude DAG (120-192 g, 35-55%, purity 98.7% to 99.4%, n=6 lots).

The alternative t-butanol epoxidation process was difficult to scale up due to the fact that the freezing point of t-butanol is approximately 10° C. Although the preferred base for this process is $K_2CO_3$, other bases, such as N,N-diisopropylethylamine (DIPEA), triethanolamine (TEA), or 1,8-diazabicycloundec-7-ene (DBU) can alternatively be used. However, as indicated, it is preferable to use $K_2CO_3$. Additionally, if $K_2CO_3$ is used as the base, the solvent can be dimethylformamide (DMF) or tetrahydrofuran (THF). However, it is preferable to use THF.

For the fourth step of the process (step (iv), recrystallization of dianhydrogalactitol), the reaction vessel is a nitrogen-purged 12-L three-neck round-bottom flask equipped with a magnetic stirrer, nitrogen thermometer, and condenser. Crude dianhydrogalactitol (977.5 g) was charged into the reaction flask at ambient temperature. Acetone (25 parts) was charged into the reaction flask at ambient temperature and agitation was started. The reaction mixture, which was slightly cloudy, was agitated at room temperature for 30 minutes. The insoluble solids were filtered off and the acetone filtrate was collected. The acetone filtrate was charged back into the reaction flask, cleaned by water and acetone. The acetone filtrate was then concentrated to about 1.5-2 parts under vacuum with the jacket temperature being set at 30° C. The reaction mixture is then cooled down to −20° C. over 4 hours and then the white suspension is agitated at −20° C. for 24 hours. The solids are filtered and washed with 2×1.5 parts of MTBE. The solids are dried at ambient temperature under nitrogen and vacuum for about 6-18 hours. The yield was 901.4 g of dianhydrogalactitol. The purity was 99.91%. Detectable impurities included 0.05% of an impurity with a relative retention time (RRT) of 0.72, which was identified as 1,2-anhydrogalactitol, and 0.04% of an impurity with an RRT of 1.66, which was identified as 1,2-anhydrogalactitol-6-acetate. The preparation had 3200 ppm of acetone and 75 ppm of MTBE. Tetrahydrofuran was not detectable. The pH at 20 mg/mL was 8.0.

In another alternative, n-heptane was used for the isolation of dianhydrogalactitol. However, when n-heptane was used, impurities were also co-precipitated and it was difficult to remove the impurities from the DAG product. Additionally, cooling the concentrated THF reaction mixture to 0° C. produced high-purity DAG but the quantity of THF remaining was too high to be effectively removed by longer drying. This issue was resolved by recrystallization from acetone.

Typically, the purity of the resulting product is monitored by HPLC. In one alternative, HPLC is performed on a YMC Pack Pro C18 column (YMC America, Allentown, Pa.), with a mobile phase of 0.1% formic acid-water-acetonitrile). Alternatively, the mobile phase can employ a water/acetonitrile gradient with no formic acid. Typically, for HPLC detection, electrospray detection is employed. Alternatively, refractive index (RI) detection can be employed.

Other methods known in the art, including epoxide titration and thin-layer chromatography, can be used to determine the purity of the resulting product.

Essentially the same method can be used on an even larger scale, such as 14 kg of dulcitol+40 kg of 33% hydrobromic acid, yielding about 8.8 kg of crude dianhydrogalactitol and 1.43 kg of pure dianhydrogalactitol.

In general, as applied to the synthesis of a dianhydrohexitol, this alternative, scalable, version of the process comprises the steps of:

(1) converting a hexitol to a dibromo derivative of the hexitol by reaction of the hexitol with hydrobromic acid for from about 12 hours to about 36 hours at an elevated temperature, wherein the hydrobromic acid is at a concentration of from about 30% to about 35%, and wherein the elevated temperature is from about 35° C. to about 45° C.;

(2) precipitating the product of step (1) with water;

(3) washing the precipitated product of step (2) with an aliphatic ether;

(4) drying the washed product of step (3) under nitrogen and vacuum;

(5) converting the dibromo derivative of the hexitol from step (4) to the dianhydro derivative thereof by reacting with a base selected from the group consisting of potassium carbonate, N,N-diisopropylethylamine (DIPEA), triethanolamine (TEA), and 1,8-diazabicycloundec-7-ene (DBU) in a polar aprotic solvent at a temperature of from about 35° C. to 45° C. for from about 16 hours to about 20 hours;

(6) washing the product of step (5) with tetrahydrofuran and then with water; and (7) recrystallizing the product of step (6) from an aliphatic ketone to produce a dianhydro derivative of the hexitol.

In this process, the starting material (the hexitol) is preferably dulcitol. When the starting material is dulcitol, the dibromo derivative of the hexitol is dibromodulcitol and the dianhydro derivative of the hexitol is dianhydrogalactitol.

In this process, in step (1), the hydrobromic acid is preferably at a concentration of about 33%. In step (1), the elevated temperature is typically from about 37.5° C. to about 42.5° C. In step (1), the elevated temperature is preferably at about 40° C. In this process, in step (1), the reaction time is typically from about 12 hours to about 24 hours, such as 18 hours or 24 hours. The reaction time may also be from about 12 hours to about 18 hours.

In this process, in step (3), typically the aliphatic ether is selected from the group consisting of methyl t-butyl ether, dimethyl ether, methyl ethyl ether, diethyl ether, dipropyl ether, methyl propyl ether, and ethyl propyl ether. Preferably, the aliphatic ether is methyl t-butyl ether.

In this process, in step (5), preferably the base is potassium carbonate. In this process, in step (5), typically the polar aprotic solvent is selected from the group consisting of dimethylformamide and tetrahydrofuran. Preferably, the polar aprotic solvent is tetrahydrofuran.

In this process, in step (5), typically, the temperature is from about 37.5° C. to about 42.5° C. Preferably, the temperature is about 40° C.

In this process, in step (5), typically, the duration of the reaction is from about 17 hours to about 19 hours. Preferably, the duration of the reaction is about 18 hours.

In this process, in step (7), typically the aliphatic ketone is selected from the group consisting of diethyl ketone and acetone. Preferably, the aliphatic ketone is acetone.

When the product of the synthesis process is dianhydrogalactitol, typically the dianhydrogalactitol resulting from step (7) of the synthesis process is at a purity of at least 99.80%. Preferably, the dianhydrogalactitol is at a purity of about 99.91%. Typically, when the product of the synthesis process is dianhydrogalactitol, the dianhydrogalactitol contains less than 3500 ppm of the aliphatic ketone used for recrystallization in step (7), such as acetone. Preferably, when the product of the synthesis process is dianhydrogalactitol, the dianhydrogalactitol contains less than 3200 ppm of the aliphatic ketone used for recrystallization in step (7), such as acetone. Typically, when the product of the synthesis process is dianhydrogalactitol, the dianhydrogalactitol contains less than 90 ppm of the aliphatic ether used as a solvent in step (3), such as MTBE. Preferably, when the product of the synthesis process is dianhydrogalactitol, the dianhydrogalactitol contains less than 75 ppm of the aliphatic ether used as a solvent in step (3), such as MTBE. Preferably, when the product of the synthesis process is dianhydrogalactitol, the dianhydrogalactitol contains no detectable amount of the polar aprotic solvent used in step (5), such as THF.

Another aspect of the invention is purified recrystallized dianhydrogalactitol prepared by the method described above (with steps (1)-(7)). Typically, the dianhydrogalactitol is at a purity of at least 99.80%. Preferably, the dianhydrogalactitol is at a purity of about 99.91%. Typically, the dianhydrogalactitol contains less than 3500 ppm of the aliphatic ketone used for recrystallization in step (6), such as acetone. Preferably, the dianhydrogalactitol contains less than 3200 ppm of the aliphatic ketone used for recrystallization in step (6). Typically, the dianhydrogalactitol contains less than 90 ppm of the aliphatic ether used as a solvent in step (3), such as MTBE. Preferably, the dianhydrogalactitol contains less than 75 ppm of the aliphatic ether as a solvent in step (3).

Typically, the dianhydrogalactitol contains no detectable amount of the polar aprotic solvent used in step (5), such as THF.

Conventional analytical techniques can be used to monitor the reaction at each step and to determine the purity of the final product as well as identify any impurities. Suitable analytical techniques are described in United States Patent Application Publication No. 2014/0315318 by Lu et al., incorporated herein by this reference, and include, but are not limited to, HPLC, including HPLC with evaporative light scattering detection (ELSD); the HPLC can be followed by tandem mass spectroscopy. Suitable HLPC columns and mobile phases are disclosed therein and known in the art. Either gradient or isocratic elution can be used. Methods for ELSD and tandem mass spectroscopy are disclosed therein and are known in the art. Other alternatives for monitoring and determination are described above.

Yet another aspect of the invention is a pharmaceutical composition comprising:

(a) a therapeutically effective quantity of the purified recrystallized dianhydrogalactitol prepared by the method described above (with steps (1)-(7)); and (b) at least one pharmaceutically acceptable carrier, diluent, or excipient.

Suitable pharmaceutically acceptable carriers, diluents, and excipients are well-known in the art. The pharmaceutically acceptable carriers, diluents, and excipients can include, but are not necessarily limited to, calcium carbonate, calcium phosphate, various sugars or types of starch, cellulose derivatives, gelatin, vegetable oils, polyethylene glycols and physiologically compatible solvents. Other pharmaceutical excipients are well known in the art. Exemplary pharmaceutically acceptable carriers include, but are not limited to, any and/or all of solvents, including aqueous and non-aqueous solvents, buffers, preservatives, solid fillers, excipients, diluents, dispersion media, coatings, antibacterial and/or antifungal agents, isotonic agents, absorption delaying agents, and/or the like. Still other pharmaceutically acceptable carriers, diluents, and excipients are known in the art and can be used.

The invention is illustrated by the following Examples. These examples are for illustrative purposes only, and are not intended to limit the invention.

EXAMPLES

Comparative Example 1

This is a comparative example assessing alternatives for conversion of dulcitol to dibromodulcitol. The alternatives include: 1) reaction with 48% aqueous hydrobromic acid at about 80° C. at atmospheric pressure; for 18 hours; (2) reaction with 48% aqueous hydrobromic acid at about 90° C. in a sealed vessel for 5 hours; (3) reaction with 48% aqueous hydrobromic acid at about 90° C. in a sealed vessel for 5 hours; (4) reaction with 33% hydrobromic acid in acetic acid at 40° C. at atmospheric pressure for 3-4 hours, followed by cooling to room temperature, addition of water, and filtration; (5) reaction with 33% hydrobromic acid in acetic acid at 80° C. in a sealed vessel for 18 hours, followed by cooling to room temperature; (6) reaction with 33% hydrobromic acid in acetic acid at 40° C. at atmospheric pressure for 3-4 hours, followed by cooling to room temperature, addition of water, and filtration.

Of these alternatives, only alternatives (4) and (6) provided substantially complete conversion of dulcitol to dibromodulcitol. The reaction did not work without pressure with aqueous solution (48%) HBr. With higher temperatures (90° C.) some conversion of starting material to the desired product was observed. As expected, elimination of water from the bromination reaction appears to have improved the efficiency of the conversion of dulcitol to dibromodulcitol. With the use of HBr in HOAc, the conversion of dulcitol was complete at 40° C. Elevated temperatures and pressure with HOAc appeared to cause degradation. $^1$H-NMR and $^{13}$C-NMR confirmed that the product was dibromodulcitol.

In yet another alternative for the conversion of dulcitol to dibromodulcitol, ducitol and hydrobromic acid were heated in HOAc solution for 4 hours at about 40° C. and then allowed to react for another 18 hours at room temperature. The reaction vessel was charged with 8 parts of toluene and concentrated to 5 parts (×2). Solids were observed, and the mixture was stirred at room temperature. This resulted in the complete removal of HOAc.

Other alternatives have been demonstrated for the isolation and work-up of dibromodulcitol. These included: (1) heating dulcitol with 2 equivalents of hydrobromic acid at 40° C. for 18 hours, then quenching the reaction mixture with 1 part of water and cooling at 4° C. for 18 hours; (2) taking dulcitol with 2 parts of HOAc and slowly adding HBr solution at room temperature and then heating at 40° C. for 18 hours, quenching with 4 parts of water and cooling at 4° C. for 18 hours; (3) heating dulcitol with 3 equivalents of hydrobromic acid at 40° C. for 18 hours, then quenching the reaction mixture with 1 part of water, generating an oil, and cooling at 4° C. for 18 hours; (4) heating dulcitol with 3 equivalents of hydrobromic acid at 40° C. for 18 hours, then quenching the reaction mixture with sodium acetate at room temperature; (5) heating together with 2.2 equivalents of hydrogen bromide and 2.2 equivalents of potassium bromide at 40° C. for 18 hours, then quenching with 10 parts of water at room temperature and stirring for 6 hours at room temperature; (6) stirring together with 2.2 equivalents of hydrogen bromide and 5.0 equivalents of lithium bromide at room temperature for 48 hours, then quenching with 10 parts of water at room temperature and stirring for 12 hours at room temperature and then at 4° C. for 18 hours; (7) stirring together with 2.1 equivalents of hydrogen bromide at room temperature for 48 hours, and then quenching with 10 parts of cold water and keeping at 4° C. for 18 hours; (8) stirring together with 2.1 equivalents of hydrogen bromide at room temperature for 48 hours, and then quenching with 10 parts of MTBE at room temperature and then stirred for 6 hours at room temperature; and (9) stirring together with 2.1 equivalents of hydrogen bromide at room temperature for 48 hours, and then quenching with 10 parts of toluene at room temperature and then stirred for 6 hours at room temperature. The yields for these were: 35%, with one impurity, for (1); 16%, with one impurity, for (2); 15%, with one impurity, for (3); undeterminable for (4) because of the formation of an unanalyzable oil; 38%, with one impurity, for (5); 35% for (6); 42%, with one impurity (at a lower concentration than other processes), for (7); 45%, with one impurity, for (8); and 50%, with one impurity, for (9). The impurity has been tentatively identified as a compound of Formula (II):

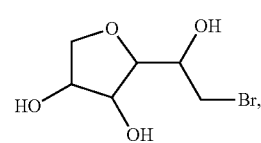

(II)

based on $^{13}$C resonance.

Additional alternatives for the conversion of dulcitol to dibromodulcitol, scaled up to 50 grams, were: (1) dulcitol is taken into a flask and hydrogen bromide solution added very slowly from an addition funnel, stirred at room temperature for 18 hours, charged with 3 parts of deionized water and stirred at room temperature for 2 hours, then filtered, washed with water, and dried, with a yield of 20%; (2) dulcitol is taken into a flask and cold hydrogen bromide solution added in one portion, stirred at room temperature for 18 hours, charged with 5 parts of cold deionized water and stirred at 5° C. for 2 hours, then filtered, washed with cold water, and dried, with a yield of 20%; (3) dulcitol is taken into a flask and hydrogen bromide solution added in one portion at room temperature, stirred at 40° C. for 18 hours, charged with 2 parts of deionized water at room temperature and stirred for 24 hours, filtered, washed with water, and dried, with a yield of 40%; (4) dulcitol is taken into a flask and hydrogen bromide solution added in one portion at room temperature, stirred at 65° C. to 70° C. for 18 hours, charged with 2 parts of MTBE at room temperature and stirred for 2 hours, then filtered, washed with MBTE, and dried (degradation occurred by IPC); and (5) dulcitol is taken into a flask and hydrogen bromide solution added in one portion at room temperature, stirred at 60° C. to 62° C. for 4 hours, charged with 2 parts of deionized water at room temperature and stirred for 18 hours, filtered, washed with water, and dried, with a yield of 30%. One impurity was determined in (1), (2), (3), and (5).

Further scale-up to 3 kilograms of starting material included: (1) dulcitol is stirred with hydrogen bromide solution at 40° C. for 18 hours, then cooled to room temperature and stirred for 18 hours, then the solids were filtered and dried to get stirrable solids over a 5-day period, washed with MBTE and dried under nitrogen with suction at room temperature over 60 hours; the yield was 1.72 kg (35%), and the purity of the dibromodulcitol was 89%.

Comparative Example 2

This is a comparative example assessing alternatives for conversion of dibromodulcitol to dianhydrogalactitol. These alternatives include: (1) use of acetone as the solvent with Ambersep (OH) resin as the base, heated together in a vial at 40° C. for 2 hours and then at room temperature at 18 hours; the starting material was insoluble; the filtrate was filtered and analyzed, resulting in some product and unreacted starting material by $^{13}$C-NMR; (2) use of t-butanol as the solvent with potassium carbonate as the base, heated together in a vial at 40° C. for 2 hours and then at room temperature at 18 hours; the starting material was insoluble; the filtrate was filtered and analyzed, resulting in a clean conversion to dianhydrogalactitol by $^{13}$C-NMR; (3) use of tetrahydrofuran as the solvent with potassium carbonate as the base, heated together in a vial at 40° C. for 2 hours and then at room temperature at 18 hours; the starting material was insoluble; the filtrate was filtered and analyzed, resulting in a clean conversion to dianhydrogalactitol by $^{13}$C-NMR; (4) use of DMF as the solvent with DIPEA as the base, stirred together in a vial at room temperature (products not isolatable); (5) use of DMF as the solvent with TEA as the base, stirred together in a vial at room temperature (products not isolatable); (6) use of DMF as the solvent with DBU as the base, stirred together in a vial at room temperature (products not isolatable); (7) use of DMF as the solvent with Ambersep (OH) as the base, stirred together in a vial at room temperature (products not isolatable); (8) use of THF as the solvent with DIPEA as the base, stirred together in a vial at room temperature; the solids were analyzed by $^{13}$C-NMR, indicating that only the starting material was present as a solid; the filtrate was concentrated to dryness and also analyzed by $^{13}$C-NMR, indicating no dianhydrogalactitol; the mono-epoxide may have been present; (9) use of THF as the solvent with TEA as the base, stirred together in a vial at room temperature; the solids were analyzed by a $^{13}$C-NMR, indicating that only the starting material was present as a solid; the filtrate was concentrated to dryness and also analyzed by $^{13}$C-NMR, indicating no dianhydrogalactitol; (10) use of THF as the solvent with DBU as the base, stirred together in a vial at room temperature; the solids were analyzed by $^{13}$C-NMR, indicating that only the starting material was present as a solid; the filtrate was concentrated to dryness and also analyzed by $^{13}$C-NMR, indicating some dianhydrogalactitol along with mono-epoxide; and (11) use of THF as the solvent with Ambersep (OH) resin as the base, stirred together in a vial at room temperature, filtered and the filtrate concentrated to dryness and analyzed by $^{13}$C-NMR, indicating the presence of only starting material and mono-epoxide.

Yet a further scale-up to 5 kilograms of starting material included: dulcitol is stirred with hydrogen bromide solution at 40° C. for 18 hours, then cooled to room temperature and stirred for 18 hours, then the solids were filtered and dried to get stirrable solids over a 5-day period, washed with MBTE and dried under nitrogen with suction at room temperature over 60 hours; the yield was 3.1 kg (39% yield), and the purity of the dibromodulcitol was 89%.

Comparative Example 3

This is a comparative example assessing alternatives for recrystallization of dianhydrogalactitol. The alternatives include: (1) 150 mg of crude diacetyldianhydrogalactitol (purity 88.2%) was dissolved in acetone (10 parts) and then heptane (10 parts) was added slowly to precipitate out the dianhydrogalactitol; 80-100 mg of dianhydrogalactitol was isolated with a purity of 92.6%; (2) 150 mg of crude diacetyldianhydrogalactitol (purity 78%) was dissolved in THF (10 parts) and then heptane (10 parts) was added slowly to precipitate out the dianhydrogalactitol; 80-100 mg of dianhydrogalactitol was isolated with a purity of 89%; (3) 250 mg of crude dianhydrogalactitol (purity 92.5%) was dissolved in 15 parts THF at room temperature and filtered through a capsule filter to remove undissolved particles; MTBE was added slowly with no formation of solids, then heptane (10 parts) was added slowly to precipitate out the dianhydrogalactitol, 200 mg of dianhydrogalactitol was isolated (80% recovery) with a purity of 97.14%; (4) 250 mg of crude dianhydrogalactitol (purity 92.5%) was dissolved in 15 parts acetone at room temperature and filtered through a capsule filter to remove undissolved particles; MTBE was added slowly with no formation of solids, then heptane (10 parts) was added slowly to precipitate out the dianhydrogalactitol, 200 mg of dianhydrogalactitol was isolated (80% recovery) with a purity of 97.3%; and (5) 250 mg of crude dianhydrogalactitol (purity 92.5%) was dissolved in 15 parts THF at room temperature and filtered through a capsule filter to remove undissolved particles; MTBE was added slowly with no formation of solids, then heptane (10 parts) was added slowly to precipitate out the dianhydrogalactitol, 220 mg of dianhydrogalactitol was isolated (88% recovery) with a purity of 97.3%.

Another procedure for isolation of the dianhydrogalactitol occurs in two steps: (1) slow cooling/precipitation of dianhydrogalactitol from the reaction mixture; and (2) acetone rework of the isolated dianhydrogalactitol. In the first step, 25 g of dibromodulcitol was used and the dibromodulcitol and potassium carbonate stirred in THF at 40° C. for 18 hours, cooled to room temperature, and the solids filtered off. The solids were washed with 5 parts of THF. The THF layer was concentrated to 8 parts (200 mL) and stirred at room temperature overnight. A slightly cloudy solution resulted but no solids were visible. The solution was then cooled to 0° C. slowly (over 2 hours) under stirring and the solids precipitated out; the solution was then cooled to −10° C. The yield of dianhydrogalactitol was 5.05 g (42.5% yield). The purity of the dianhydrogalactitol was 98.97%. The residual solvents were 2974 ppm of THF and 40 ppm of MTBE.

In the second step, the dianhydrogalactitol from the first step was dissolved in 25 parts of acetone to yield a slightly cloudy solution. The solution was filtered out to remove any undissolved particles and then concentrated to 2 parts (20 mL). The mixture was stored at −20° C. for 60 hours, then the solids were filtered, washed with MTBE and dried under nitrogen with suction at room temperature for 18 hours. The recovery was 9.9875 g of dianhydrogalactitol (91% yield) at a purity of 99.3%. THF as a residual solvent was not detectable; MTBE was present as a residual solvent at 26 ppm; and acetone was present as a residual solvent at 1435 ppm. The total impurities (other than residual solvents) decreased from 1.03% in the starting material to 0.70% in the dianhydrogalactitol recrystallized from acetone.

Example 1

Synthesis and Isolation of Dianhydrogalactitol

The first step is the conversion of dulcitol to dibromodulcitol. The reactor setup was a 20-L Chemglass reactor equipped with a mechanical stirrer, nitrogen inlet, thermometer and condenser. The outlet was connected to a scrubber flask containing 1N NaOH solution. To the prepared 20-L reactor was charged 33% HBr in acetic acid (2.1 eq, 2.05 parts v/w) under $N_2$ without agitation. With gentle to moderate agitation, the reactor was charged slowly with C091 (1.0 eq) as a solid and agitated for 10 min under $N_2$ at room temperature. While maintaining moderate to vigorous agitation, the slurry was heated to 40° C. (37 to 43° C.) over 60 min and then maintained at 40° C. (37 to 43° C.) for an additional 18-24 hrs. At this point, IPC #1 (reaction completion by$^{13}$C-NMR) was conducted and the reaction was held at 40° C. during this time, The reaction mixture was then cooled to room temperature over 2 hrs. The reaction mixture was then quenched with water (DI, 2 parts v/w) and the resulting thick suspension was agitated at room temperature for another 18-24 h. The thick suspension was then vacuum filtered and pulled to near dryness. The reactor was rinsed forward with water (1 part v/w) through the filter cake and pulled to near dryness. A final wash was conducted by rinsing the reactor forward with MTBE (2×1 parts v/w) through the filter cake and pulling to dryness. The product was then dried under vacuum on the filter (counter balanced with $N_2$) with occasional mixing for 60 hrs at room temperature to yield the desired product dibromodulcitol (yield 35-40%). A sample was removed for IPC #2; chemical purity, water content by Karl Fischer titration (')/0 w/w) and residual solvents (HOAc) analysis.

The next step was the conversion of the dibromodulcitol to dianhydrogalactitol by an epoxide ring-closure reaction. The reactor setup was a 12-L Jacketed round-bottom flask equipped with a mechanical stirrer, nitrogen inlet, thermometer and condenser inside an isolator. To the prepared 12 L flask was charged dibromodulcitol (1 eq) and $K_2CO_3$ (2.5 eq) as solids under $N_2$ without agitation. THF (15 parts v/w) was then charged and agitation was commenced slowly and agitated for 10 min under $N_2$ at room temperature. While maintaining vigorous agitation, the slurry was heated to 40° C. (37 to 43° C.) over 60 min and then maintained at 40° C. (37 to 43° C.) for an additional 18-24 hrs. The reaction mixture was then cooled to room temperature and a sample pulled for IPC #3 (reaction completion by HPLC/ELSD). The thick suspension was then filtered under vacuum and pulled to near dryness. The reactor was rinsed forward with THF (2×5 parts v/w) through the filter cake and pulled to near dryness. The THF filtrates were combined and concentrated down to ~2-2.5 parts (v/w) under reduced pressure (jacket temperature set at 35° C.). The white, thick suspension was cooled to −0° C. and maintained at −0° C. for another 12-18 hrs under $N_2$ with gentle agitation. The white solids were then filtered out under vacuum and washed with MTBE (2 parts v/w) and pulled to dryness. The product was then dried under vacuum (counterbalanced with $N_2$) with occasional mixing for 6-12 hrs at room temperature to yield the crude dianhydrogalactitol (yield 40-50%). A sample was removed for purity analysis by HPLC.

The final step was the recrystallization of crude dianhydrogalactitol. The reactor setup was a 12-L Jacketed round bottom flask equipped with a mechanical stirrer, nitrogen inlet, thermometer and condenser inside an isolator. The crude dianhydrogalactitol was charged into the 12-L reactor under nitrogen at room temperature without agitation. Then acetone (25 parts w/v) was charged at room temperature under nitrogen and agitation was slowly started and continued for 30-40 min at room temperature to dissolve most of the solids. The solution was then vacuum filtered through a Buchner funnel to remove any undissolved solids. Then the filtrate was charged back into the flask and concentrated down to ~1.5-2.0 parts (jacket temperature set at 35° C.). The thick, white suspension was cooled to −20° C. and maintained at −20° C. for another 12-18 hrs under $N_2$ with gentle agitation. The white solids were then collected by vacuum filtration. The reactor was rinsed forward with MTBE (2 parts v/w) through the filter cake and pulled to dryness. The product was then dried under vacuum (counterbalanced with $N_2$) with occasional mixing for 6-12 hrs at room temperature to yield the pure dianhydrogalactitol (recovery yield 90-92%). A sample was removed for analysis. The product contained the following residual solvents: 3228 ppm of acetone, no detectable tetrahydrofuran, and a trace (<500 ppm) of MTBE. The HPLC purity assay was 99.9%.

In the overall procedure, it is preferred to charge the potassium carbonate as a solid in portions to a stirring suspension of dibromodulcitol in THF to prevent possible breakage of the stirring shaft. Additionally, the total water content of the dibromodulcitol and potassium carbonate is significant for reaction completion; when the total water content was <6% w/w by Karl Fischer titration, the reaction stalled. Therefore, it is preferable that the water content must be adjusted (if required) to ensure that the combined water content for dibromodulcitol and potassium carbonate is 6-7% (w/w).

The disappearance of dulcitol at IPC #1 is shown by $^{13}$C-NMR in FIG. 1.

Figure 2:
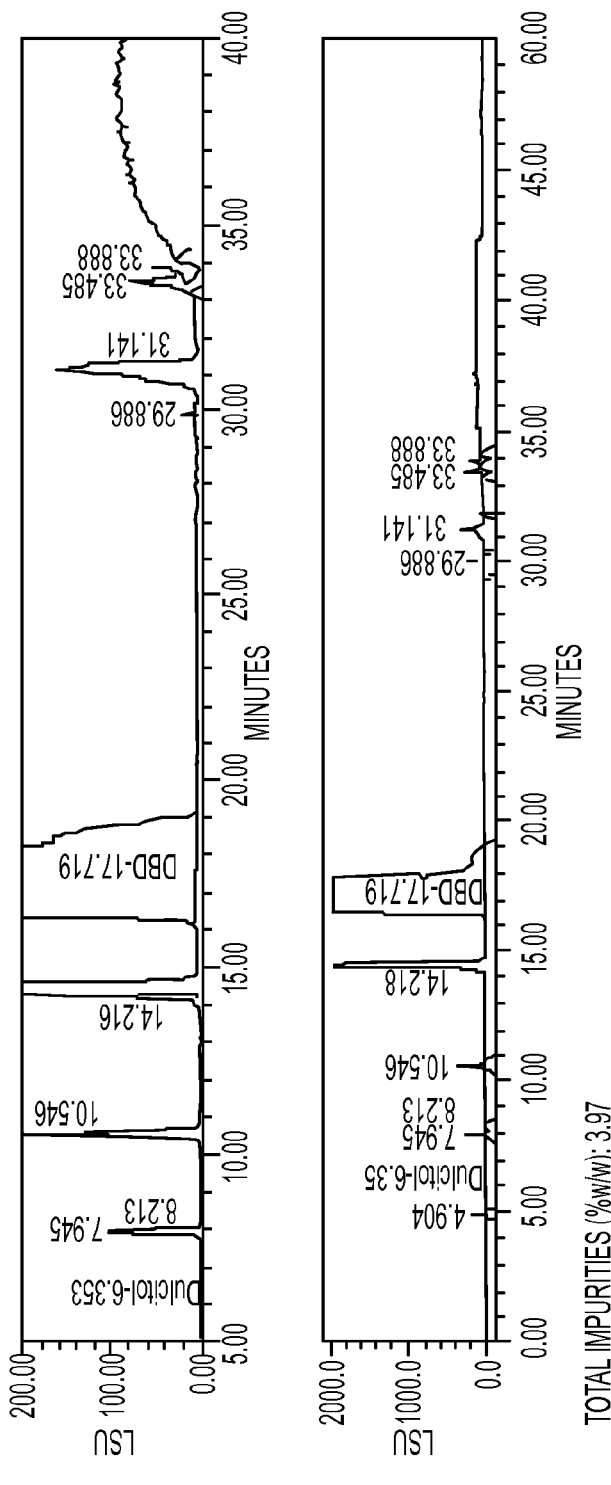
FIG. 2 shows an HPLC chromatogram for the conversion of dulcitol to dibromodulcitol in Example 1. Detection was by ELSD. The injection volume was 50 μL.

An HPLC chromatogram for the conversion of dulcitol to dibromdulcitol is shown in FIG. 2. Detection was by ELSD. The injection volume was 50 µL.

Figure 3:
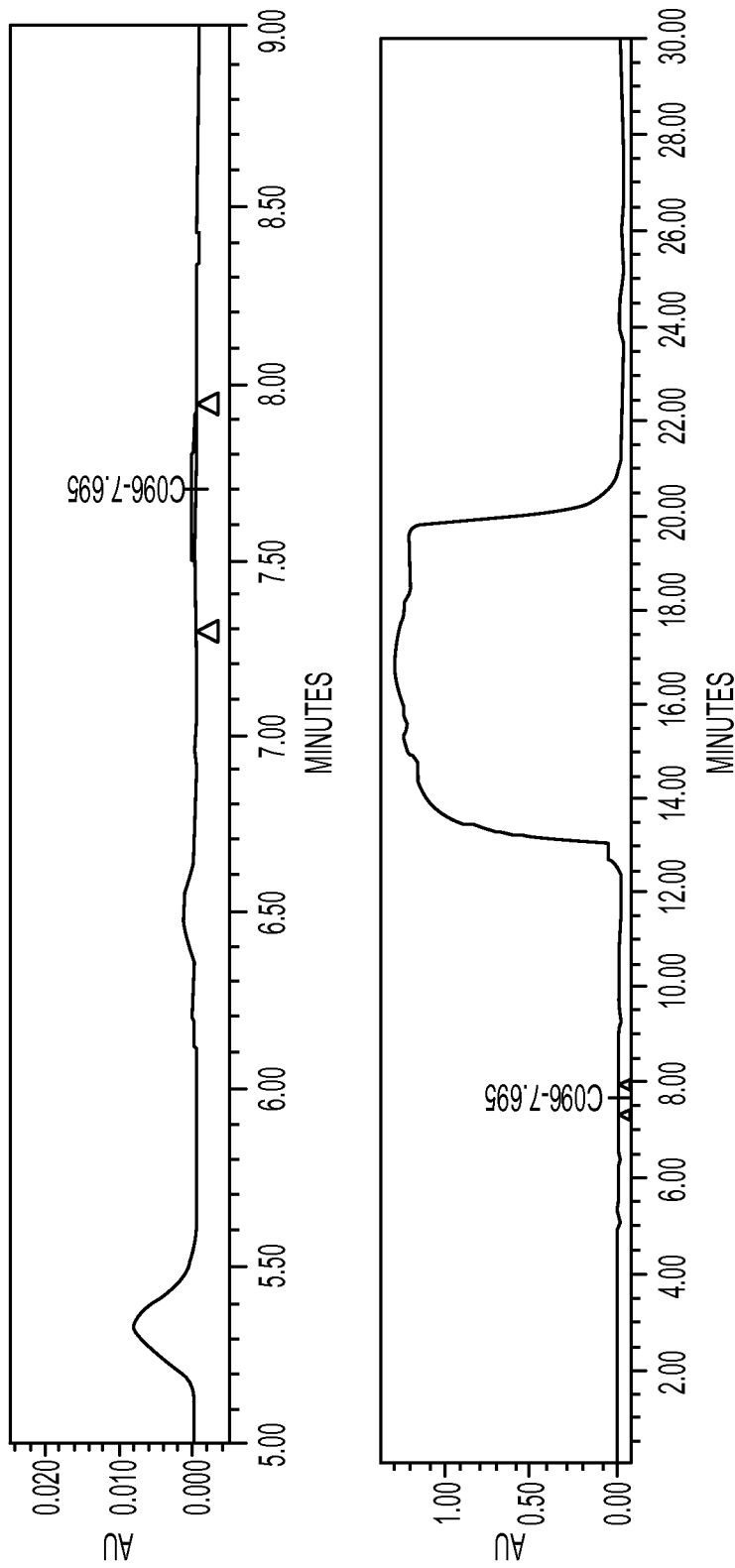
FIG. 3 shows an HPLC chromatogram for the conversion of dibromodulcitol to dianhydrogalactitol in Example 1. Detection was by ELSD. The injection volume was 10 μL.

An HPLC chromatogram for the conversion of dibromodulcitol to dianhydrogalactitol is shown in FIG. 3. Detection was by ELSD. The injection volume was 10 μL.

Figure 4:
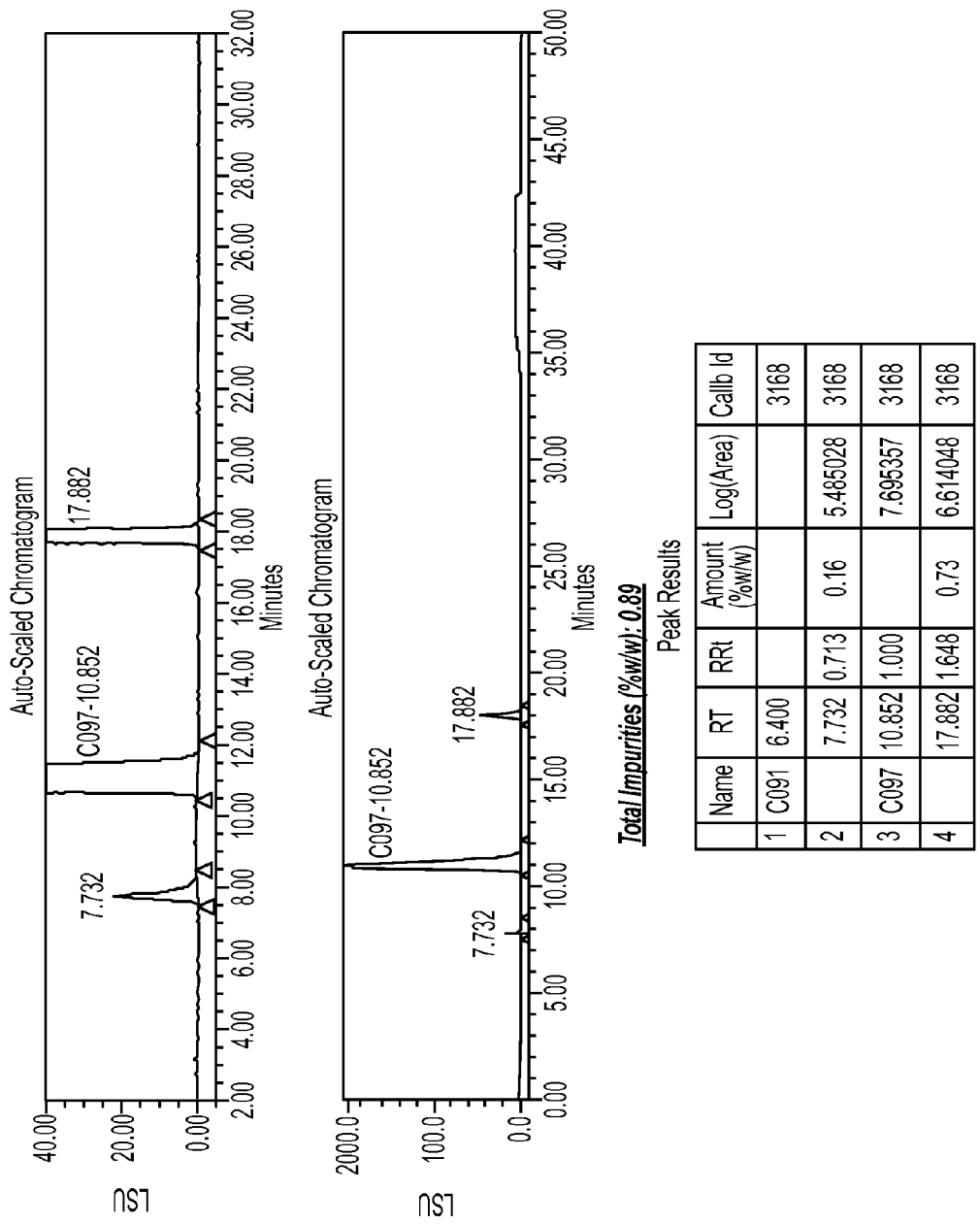
FIG. 4 shows an HPLC chromatogram for crude dianhydrogalactitol in Example 1. Detection was by ELSD. The injection volume was 100 μL.

An HPLC chromatogram for the crude dianhydrogalactitol is shown in FIG. 4. Detection was by ELSD. The injection volume was 100 μL.

Figure 5:
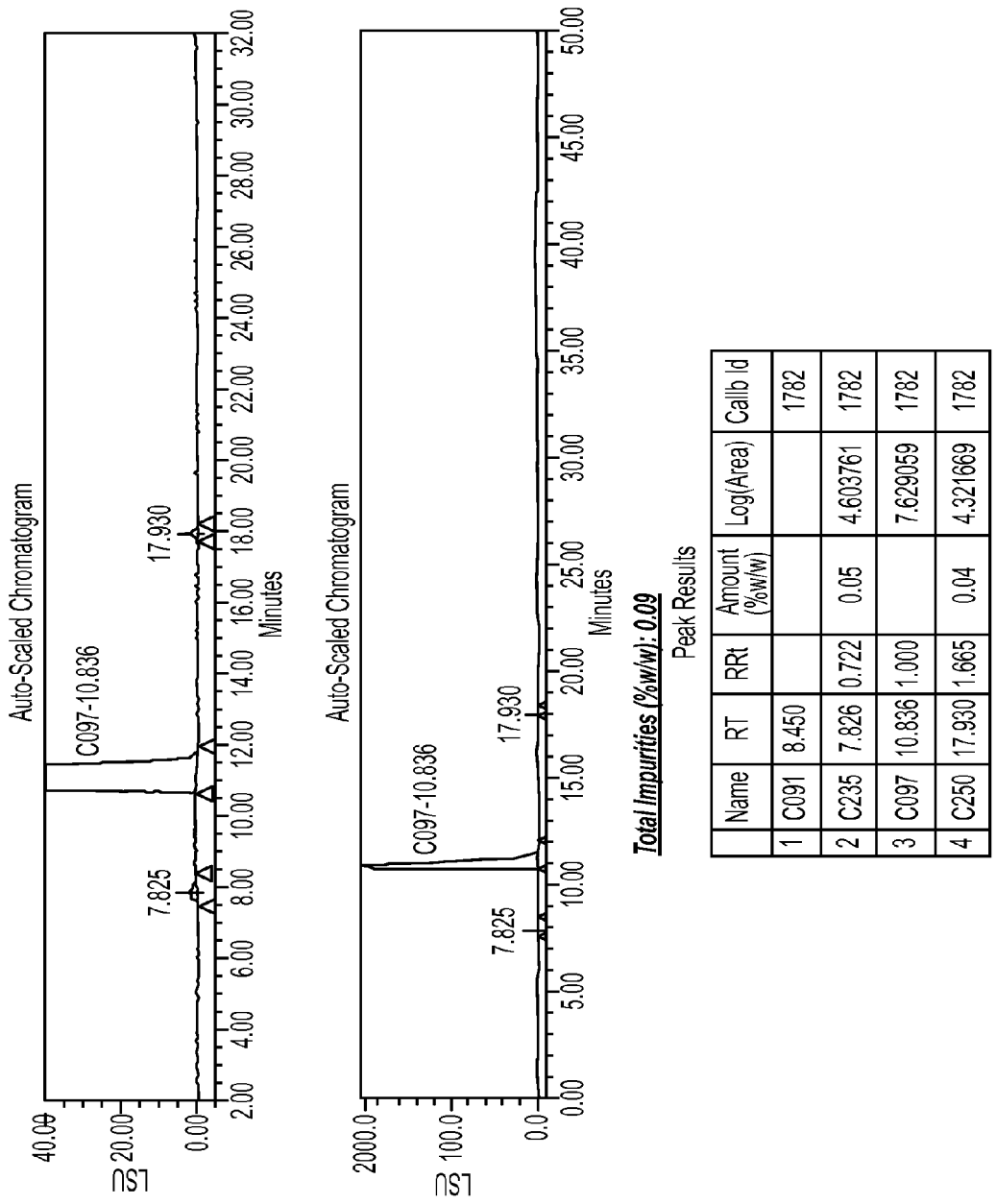
FIG. 5 shows an HPLC chromatogram for purified dianhydrogalactitol in Example 1. Detection was by ELSD. The injection volume was 100 μL.

An HPLC chromatogram for purified dianhydrogalactitol is shown in FIG. 5. Detection was by ELSD. The injection volume was 100 μL.

To summarize analytical results, the purified dianhydrogalactitol was a white solid. The infrared spectrum conforms to the reference standard. The HPLC retention time is ±5% of the standard. Total impurities were <0.1% (w/w) and dulcitol was not detectable. In a chromatographic assay (HPLC/RI), the purity was assessed at 100% ("as is"). Residual dibromodulcitol was not detected. Water content was 0.4% by Karl Fischer titration. The product contained the following residual solvents: 3228 ppm of acetone, no detectable tetrahydrofuran, and a trace (<500 ppm) of MTBE. The epoxide content was 203% (w/w). The residue on ignition was 0.01% (w/w). The X-ray powder diffraction spectrum conformed to the standard. Heavy metal content was less than 20 ppm. The compound formed a colorless, clear solution. The pH of a 20 mg/mL solution was 8.0.

These results demonstrated that the synthesis and purification of dianhydrogalactitol can be scaled up to yield high-purity dianhydrogalactitol suitable for pharmaceutical use or preparation of pharmaceutical compositions.

Advantages of the Invention

The present invention provides an improved and efficient method for the synthesis of substituted hexitols, especially dianhydrogalactitol (DAG). The method of the present invention is readily scalable so that large quantities of dianhydrogalactitol can be prepared for pharmaceutical or other use. The method of the present invention produces dianhydrogalactitol in high yield and free from impurities. In particular, the method of the invention is scalable and can be used to prepare large quantities of dianhydrogalactitol or other substituted hexitols for the preparation of drug dosages or pharmaceutical compositions.

Methods according to the present invention possess industrial applicability for the synthesis of substituted hexitols, especially dianhydrogalactitol (DAG), which have uses in pharmacology and elsewhere. Compositions according to the present invention possess industrial applicability as pharmaceutical compositions.

With respect to ranges of values, the invention encompasses each intervening value between the upper and lower limits of the range to at least a tenth of the lower limit's unit, unless the context clearly indicates otherwise. Moreover, the invention encompasses any other stated intervening values and ranges including either or both of the upper and lower limits of the range, unless specifically excluded from the stated range.

Unless defined otherwise, the meanings of all technical and scientific terms used herein are those commonly understood by one of ordinary skill in the art to which this invention belongs. One of ordinary skill in the art will also appreciate that any methods and materials similar or equivalent to those described herein can also be used to practice or test this invention.

The publications and patents discussed herein are provided solely for their disclosure prior to the filing date of the present application. Nothing herein is to be construed as an admission that the present invention is not entitled to antedate such publication by virtue of prior invention. Further the dates of publication provided may be different from the actual publication dates which may need to be independently confirmed.

All the publications cited are incorporated herein by reference in their entireties, including all published patents, patent applications, and literature references, as well as those publications that have been incorporated in those published documents. However, to the extent that any publication incorporated herein by reference refers to information to be published, applicants do not admit that any such information published after the filing date of this application to be prior art.

As used in this specification and in the appended claims, the singular forms include the plural forms. For example the terms "a," "an," and "the" include plural references unless the content clearly dictates otherwise. Additionally, the term "at least" preceding a series of elements is to be understood as referring to every element in the series. The inventions illustratively described herein can suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the future shown and described or any portion thereof, and it is recognized that various modifications are possible within the scope of the invention claimed. Thus, it should be understood that although the present invention has been specifically disclosed by preferred embodiments and optional features, modification and variation of the inventions herein disclosed can be resorted by those skilled in the art, and that such modifications and variations are considered to be within the scope of the inventions disclosed herein. The inventions have been described broadly and generically herein. Each of the narrower species and subgeneric groupings falling within the scope of the generic disclosure also form part of these inventions. This includes the generic description of each invention with a proviso or negative limitation removing any subject matter from the genus, regardless of whether or not the excised materials specifically resided therein. In addition, where features or aspects of an invention are described in terms of the Markush group, those schooled in the art will recognize that the invention is also thereby described in terms of any individual member or subgroup of members of the Markush group. It is also to be understood that the above description is intended to be illustrative and not restrictive. Many embodiments will be apparent to those of in the art upon reviewing the above description. The scope of the invention should therefore, be determined not with reference to the above description, but should instead be determined with reference to the appended claims, along with the full scope of equivalents to which such claims are entitled. Those skilled in the art will recognize, or will be able to ascertain using no more than routine experimentation, many equivalents to the specific embodiments of the invention described. Such equivalents are intended to be encompassed by the following claims.

What is claimed is:

1. A process for synthesizing and recrystallizing a dianhydrohexitol comprising the steps of:
   (a) converting dulcitol to dibromodulcitol by reaction of dulcitol with hydrobromic acid for from about 12 hours to about 36 hours at an elevated temperature, wherein the hydrobromic acid is at a concentration of from about 30% to about 35%, and wherein the elevated temperature is from about 35° C. to about 45° C.;

(b) precipitating the product of step (a) with water;

(c) washing the precipitated product of step (b) with an aliphatic ether;

(d) drying the washed product of step (c) under nitrogen and vacuum;

(e) converting the dibromodulcitol from step (d) to dianhydrogalactitol by reacting with a base selected from the group consisting of potassium carbonate, N,N-diisopropylethylamine (DIPEA), triethanolamine (TEA), and 1,8-diazabicycloundec-7-ene (DBU) in a polar aprotic solvent at a temperature of from about 35° C. to 45° C. for from about 16 hours to about 20 hours;

(f) washing the product of step (e) with tetrahydrofuran and then with water; and (g) recrystallizing the product of step (f) from an aliphatic ketone to produce dianhydrogalactitol, and wherein the dianhydrogalactitol resulting from step (g) of the process is at a purity of at least 99.80%.

2. The process of claim 1 wherein, in step (a), the hydrobromic acid is at a concentration of about 33%.

3. The process of claim 1 wherein, in step (a), the elevated temperature is from about 37.5° C. to about 42.5° C.

4. The process of claim 3 wherein, in step (a), the elevated temperature is about 40° C.

5. The process of claim 1 wherein, in step (c), the aliphatic ether is selected from the group consisting of diethyl ether, dipropyl ether, and methyl t-butyl ether.

6. The process of claim 5 wherein, in step (c), the aliphatic ether is methyl t-butyl ether.

7. The process of claim 1 wherein, in step (e), the base is potassium carbonate.

8. The process of claim 1 wherein, in step (e), the polar aprotic solvent is selected from the group consisting of dimethylformamide and tetrahydrofuran.

9. The process of claim 8 wherein, in step (e), the polar aprotic solvent is tetrahydrofuran.

10. The process of claim 1 wherein, in step (e), the temperature is from about 37.5° C. to about 42.5° C.

11. The process of claim 10 wherein, in step (e), the temperature is about 40° C.

12. The process of claim 1 wherein, in step (a), the reaction time is from about 12 hours to about 24 hours.

13. The process of claim 12, wherein, in step (a), the reaction time is about 24 hours.

14. The process of claim 1 wherein, in step (e), the duration of the reaction is from about 17 hours to about 19 hours.

15. The process of claim 14 wherein, in step (e), the duration of the reaction is about 18 hours.

16. The process of claim 1 wherein, in step (g), the aliphatic ketone is selected from the group consisting of diethyl ketone and acetone.

17. The process of claim 15 wherein, in step (g), the aliphatic ketone is acetone.

18. The process of claim 1 wherein the dianhydrogalactitol resulting from step (g) of the process is at a purity of about 99.91%.

19. The process of claim 1 wherein the dianhydrogalactitol resulting from step (g) of the process contains less than 3500 ppm of the aliphatic ketone used for recrystallization in step (g).

20. The process of claim 19 wherein the aliphatic ketone used for recrystallization in step (g) is acetone.

21. The process of claim 20 wherein the dianhydrogalactitol resulting from step (g) of the process contains less than 3200 ppm of the aliphatic ketone used for recrystallization in step (g).

22. The process of claim 1 wherein the dianhydrogalactitol resulting from step (g) of the process contains less than 90 ppm of the aliphatic ether used as a solvent in step (c).

23. The process of claim 22 wherein the aliphatic ether used as a solvent in step (c) is MTBE.

24. The process of claim 22 wherein the dianhydrogalactitol resulting from step (g) of the process contains less than 75 ppm of the aliphatic ether used as a solvent in step (c).

25. The process of claim 24 wherein the aliphatic ether used as a solvent in step (c) is MTBE.

26. The process of claim 1 wherein the dianhydrogalactitol resulting from step (g) of the process contains no detectable amount of the polar aprotic solvent used in step (e).

27. The process of claim 26 wherein the polar aprotic solvent used in step (e) is THF.

* * * * *